(12) United States Patent
Lim et al.

(10) Patent No.: US 11,466,254 B2
(45) Date of Patent: Oct. 11, 2022

(54) COMPOSITION CONTAINING, AS ACTIVE INGREDIENT, CULTURE OF CHICKEN BONE MARROW-DERIVED OSTEOCHONDRAL PROGENITOR CELLS FOR PROMOTING OSTEOGENESIS OR INDUCING CHONDROGENIC DIFFERENTIATION

(71) Applicant: SEOUL NATIONAL UNIVERSITY R & DB FOUNDATION, Seoul (KR)

(72) Inventors: Jeong Mook Lim, Seoul (KR); Ji Yeon Ahn, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 377 days.

(21) Appl. No.: 16/757,335

(22) PCT Filed: Oct. 16, 2018

(86) PCT No.: PCT/KR2018/012200
§ 371 (c)(1),
(2) Date: Apr. 17, 2020

(87) PCT Pub. No.: WO2019/078587
PCT Pub. Date: Apr. 25, 2019

(65) Prior Publication Data
US 2021/0187035 A1    Jun. 24, 2021

(30) Foreign Application Priority Data
Oct. 18, 2017  (KR) .................. 10-2017-0135443
Oct. 18, 2017  (KR) .................. 10-2017-0135444

(51) Int. Cl.
*A61K 35/12*      (2015.01)
*A61K 35/28*      (2015.01)
*C12N 5/077*      (2010.01)

(52) U.S. Cl.
CPC ........ *C12N 5/0654* (2013.01); *C12N 2500/80* (2013.01); *C12N 2506/1353* (2013.01); *C12N 2506/1384* (2013.01)

(58) Field of Classification Search
CPC ............................... A61K 35/12; A61K 35/28
USPC ................................. 424/93.7, 577
See application file for complete search history.

(56) References Cited

U.S. PATENT DOCUMENTS

2011/0301249 A1    12/2011  Challakere

FOREIGN PATENT DOCUMENTS

KR        10-1695140 B1     1/2017

OTHER PUBLICATIONS

Chang et al., "Co-culture of chondrocytes and bone marrow mesenchymal stem cells in vitro enhances the expression of cartilaginous extracellular matrix components", Brazilian Journal of Medical and Biological Research, 2011, 44(4), pp. 303-310.
Hwang et al., "Enhanced Chondrogenesis by Three-dimensional Co-culture of Chon Chondrocytes and Mesenchymal Stem Cells", Korean Society for Biotechnology and Bioengineering Journal, 2016, vol. 31(2), pp. 120-125.
Hwang, "Enhanced Chondrogenesis by Three-dimensional Co-culture of Chondrocytes and Mesenchymal Stem Cells", INHA University, biotechnology, a master's thesis, 2015, pp. 1-47.
Khatri et al., "Isolation and differentiation of chicken mesenchymal stem cells from bone marrow", Stem Cells and Development, 2009, vol. 18(10), pp. 1485-1492.
Mo et al., "Variations in the ratios of co-cultured mesenchymal stem cells and chondrocytes regulate the expression of cartilaginous and osseous phenotype in alginate constructs", Bone, 2009, vol. 45(1), pp. 42-51 (Abstract Only).
Yang et al., "Enhanced Chondrogenesis of Osteo-Chondro Progenitor Cells Cultured in Osteogenic Medium Under Cyclic Loading", 51st Annual Meeting of the Orthopaedic Research Society, Feb. 23, 2005, Poster No. 0353.
Extended European Search Report dated Jun. 8, 2021, for corresponding EP Patent Application No. 18867602.7, 11 pages.
Heino et al., "Conditioned medium from osteocytes stimulates the proliferation of bone marrow mesenchymal stem cells and their differentiation into osteoblasts", Experimental Cell Research, 2004, vol. 294, pp. 458-468.
Pereira et al., "In vitro chondrogenic commitment of human Wharton's jelly stem cells by co-culture with human articular chondrocytes", J Tissue Eng Reen Med, 2017, vol. 11, pp. 1876-1887.
Suchorska et al., "Comparison of Four Protocols to Generate Chondrocyte-Like Cells from Human Induced Pluripotent Stem Cells (hiPSCs)", Stem Cell Rev and Rep, 2017, vol. 13, pp. 299-308.

(Continued)

*Primary Examiner* — Raymond J Henley, III
(74) *Attorney, Agent, or Firm* — Vorys, Sater, Seymour and Pease LLP; Mih Suhn Koh

(57) ABSTRACT

Provided herein are a method of promoting osteogenic differentiation efficiency of a stem cell or of inducing chondrogenic differentiation of a stem cell, comprising treating the stem cell with a culture solution of chicken bone marrow-derived osteochondroprogenitor cells; a method of preventing or treating cartilage damage or a cartilage defect disease comprising administering to a subject in need thereof a composition comprising a differentiation-induced stem cell or differentiated chondrocyte made by said method as an active ingredient; and a method of preventing or treating a bone disease, cartilage damage, or a cartilage defect disease comprising administering to a subject in need thereof, a composition comprising a culture solution or culture concentrate of chicken bone marrow-derived osteochondroprogenitor cells as an active ingredient.

9 Claims, 16 Drawing Sheets

Specification includes a Sequence Listing.

(56) References Cited

OTHER PUBLICATIONS

Zhao et al., "Chondrogenesis by bone marrow-derived mesenchymal stem cells grown in chondrocyte-conditioned medium for auricular reconstruction", J Tissue Eng Regen Med, 2017, vol. 11, pp. 2763-2773.

ODI: osteogenic differentiation inducer
CC: culture concentrate of chicken osteochondroprogenitor cells CDI: chondrogenic differentiation inducer
CC: culture concentrate of chicken osteochondroprogenitor cells

COMPOSITION CONTAINING, AS ACTIVE INGREDIENT, CULTURE OF CHICKEN BONE MARROW-DERIVED OSTEOCHONDRAL PROGENITOR CELLS FOR PROMOTING OSTEOGENESIS OR INDUCING CHONDROGENIC DIFFERENTIATION

CROSS-REFERENCE TO RELATED APPLICATIONS

This application is a 371 of PCT/KR2018/012200, filed Oct. 16, 2018, which claims the benefit of priority from Korean Patent Application No. 10-2017-0135443, filed Oct. 18, 2017 and Korean Patent Application No. 10-2017-0135444, filed Oct. 18, 2017, the contents of each of which are incorporated herein by reference in its entirety.

SEQUENCE LISTING

The Sequence Listing submitted in text format (.txt) filed on Apr. 17, 2020, named "SequenceListing.txt", created on Apr. 15, 2020 (2.62 KB), is incorporated herein by reference.

TECHNICAL FIELD

The present invention relates to a composition for promoting osteogenesis or inducing chondrogenic differentiation, and more particularly to a composition for promoting osteogenesis or inducing chondrogenic differentiation, which includes, as an active ingredient, a culture solution of chicken bone marrow-derived osteochondroprogenitor cells, and the like.

BACKGROUND ART

The cells that make up bone include osteocytes which maintain the homeostasis of bone, osteoblasts which form bone, osteoclasts which resorb bone, chondrocytes which are responsible for joint function at the distal end of bone, and the like, and even in the bone where growth is completed, spongy bone is reformed by which, when it is resorbed by osteoclasts, new bone is formed by osteoblasts at other surfaces. When the balance between bone formation and bone resorption is broken, it progresses to bone diseases, and among these bone diseases, intractable bone diseases include osteoporosis, non-union fractures, osteonecrosis, osteomalacia, bone defects, and the like. In addition, avascular necrosis of the femoral head is an intractable bone disease in which blood supply to the femoral head constituting hip joints is stopped due to trauma, drinking, taking steroids, and the like, resulting in bone destruction, and the annual incidence rate of this disease is 20,000 in the U.S. and 4,000-5,000 in Korea, and it is known that most cases occur at the age of 20-50 years and a high incidence rate is shown in the late 30s on average. However, no specific treatment method has been developed other than a surgical method such as artificial joint replacement.

In addition, osteoporosis is a condition where the density of bones is significantly reduced compared to normal people and refers to a metabolic bone disease in which a quantitative reduction in components of the bone is a main lesion. In general, the condition of osteoporosis itself is often asymptomatic or mild, but treatment thereof is generally difficult once a fracture occurs, and it is difficult to recover sufficiently even after an osteosynthesis procedure.

To date, as an agent for preventing and/or treating bone diseases, calcium preparations, estrogen preparations, selective estrogen receptor modulators (SERMs), active vitamin D3 preparations, vitamin K preparations, ipriflavone preparations, calcitonin preparations, bisphosphonate preparations, parathyroid hormone preparations, anabolic hormone preparations, bone morphogenetic protein (BMP) factors, fibroblast growth factors (FGP), and the like have been clinically used, or clinical applications have been attempted. However, despite the use of numerous drugs, the number of patients with bone diseases is increasing every year, and therefore, there is an urgent need to develop a novel therapeutic agent for efficiently treating these intractable bone diseases.

In accordance with the above-described need, studies related to biomimetic substances, gene-based therapies, and cell-based therapies, which promote bone regeneration, are actively being conducted. Among these, research related to cell-based therapies, which use mesenchymal stem cells, is actively ongoing due to characteristics of mesenchymal stem cells which can proliferate in vitro, and suitability of mesenchymal stem cells which have immunomodulatory properties.

Mesenchymal stem cells (MSCs), which are a type of adult stem cells with adherence properties, are stem cells with multipotency which are able to differentiate into osteocytes, chondrocytes, adipocytes, myocytes, nerve cells, and cardiomyocytes (Korean Patent Publication No. 10-2015-0069375). Adult stem cells can be obtained from a patient's own body, are free from ethical issues related to cell acquisition, and can differentiate into respective connective tissues such as bone tissue, cartilage tissue, adipose tissue, muscle tissue, and tendinous tissue depending on the self-replication ability and culture conditions, and thus are recognized as a very useful cell source for the regeneration of musculoskeletal tissue. Most studies on adult stem cells that have been conducted to date use mesenchymal stem cells extracted and cultured from bone marrow, and it is known that adult stem cells exist in most musculoskeletal tissues such as the periosteum, adipose tissue, and muscle. Particularly, adipose tissue can be readily obtained in large quantities without dysfunction of a donor using a relatively simple liposuction technique, and thus has recently drawn attention as a source of adult stem cells.

Adipose tissue, like bone marrow cells, originates from the embryonic mesoderm, and several studies have shown that adipose-derived adult stem cells can differentiate into bone or cartilage. However, despite the aforementioned advantages, the low differentiation potency of adipose-derived mesenchymal stem cells is considered to be a limitation in the use of adipose stem cells as a cell source. Thus, to use adipose stem cells as a useful cell source, there is a need to discover and conduct intensive research on various factors that affect the differentiation of adipose stem cells.

Meanwhile, cartilage constitutes a skeleton together with bone and serves to protect internal organs, and cartilage tissue consists of chondrocytes and a cartilage matrix surrounding the chondrocytes. Cartilage is formed by mesenchymal-derived chondroblasts, which form a matrix around the cells during the process of cell differentiation and growth. The main components of the cartilage matrix are proteoglycans and collagen (type II, type IX, and the like). It is known that proteoglycans are involved in the characteristic absorption (swelling) specific to cartilage tissue, and collagen is involved in the rigidity of cartilage against tension and shear force. In general, once cartilage tissue, which form the joints of a vertebrate, is damaged, it is not normally regenerated in vivo. When the cartilage tissue of these joints is damaged, daily activities are limited by severe pain, and when it becomes chronic, fatal degenerative arthritis occurs and thus normal life or occupational activities are interfered with. Examples of known diseases due to cartilage disorders include arthritis deformans, chondrodysplasia, degenerative disc disease, and meniscal injury.

Treatments for damaged cartilage, which have been developed to date, include chondroplasty, osteochondral transplantation, autologous chondrocyte transplantation, and the like.

The chondroplasty is the most commonly used method, which does not require direct joint incision, thus reducing the pain and burden of a patient, and enables immediate treatment of microscopic tissue damage when observed through an arthroscope. However, in chondroplasty, fibrocartilage is mainly produced, not hyaline cartilage which is required for an actual joint, and thus satisfactory effects are not obtained in terms of functionality.

Meanwhile, osteochondral transplantation is a method in which cartilage and subchondral parts, which have already been generated in a patient's normal site, are collected together, which are then transplanted into an appropriate hole made in the damaged cartilage site, and this treatment has been successful in some patients. However, this method has a problem in that a gap remains between the transplanted area and original tissue, and thus is not a complete therapy, and can be used only for patients on which autologous transplantation can be performed, and thus it cannot be a universal method.

Autologous chondrocyte transplantation, which has recently started to be performed, is a method in which chondrocytes are obtained from cartilage tissue collected from a patient's normal site and cultured and proliferated as much as necessary in vitro, which are then injected into the damaged cartilage site along with a medium via a space secured using the periosteum, allowing the cells to proliferate to fill the damaged cartilage part. However, autologous chondrocyte transplantation is complicated and difficult because donor tissue is limited and a surgery for collecting tissue for transplantation is required.

A method, in which, by applying the above method, mesenchymal stem cells (MSCs), which are chondrocyte precursor cells, are obtained from autologous mesenchymal tissue such as bone marrow, muscle, and skin, followed by differentiation in vitro, and the differentiated cells are injected into the damaged joint and cartilage sites along with a polymer, has been reported. The method of treating cartilage damage using mesenchymal stem cells obtained from adult individuals as described above involves in-vitro culture of more undifferentiated cells, and thus has showed a somewhat increased cell proliferation capacity compared to autologous chondrocyte transplantation. As factors for inducing differentiation of the mesenchymal stem cells into chondrocytes, bone morphogenetic protein (BMP), transforming growth factor β (TGF-β), fibroblast growth factor (FGF), insulin-like growth factor-I (IGF-I), and parathyroid hormone-related peptides are known. However, the differentiation factors have a problem of inducing differentiation into unwanted other cells when inducing chondrogenic differentiation of mesenchymal stem cells. That is, in the case of TGF-β, there is a risk that mesenchymal stem cells differentiate into hypertrophic chondrocytes, and in the case of BMP, there is a risk that mesenchymal stem cells differentiate into osteophytes.

Therefore, there is an urgent need for research on effective substances for inducing differentiation which have fewer side effects than existing factors for inducing chondrogenic differentiation of mesenchymal stem cells.

Meanwhile, the starter period of chickens is a period when the rate of bone growth is very fast and is a bone growth stage showing the progression of endochondral ossification in which cartilage is replaced by bone. In this period, the femurs of chickens contain a large amount of hyaline cartilage that has not yet been calcified. Endochondral ossification is a bone formation process that occurs when forming an elongated bone, i.e., long bone, in which mesenchymal stem cells inside the limb bud aggregate and differentiate into chondrocytes to produce cartilage anlage, and then chondrocytes in the central portion of the anlage selectively enlarge, calcification occurs, leading to death, and at this time, blood vessels are grown and enter thereinto and mesenchymal stem cells entering along therewith differentiate into osteoblasts (primary ossification center), thereby forming bone. This endochondral ossification process progresses from the primary ossification center to both ends of the long bone, and in the cartilage anlage, chondrocyte proliferation continues, leading to longitudinal elongation. Separate secondary ossification centers appear at both ends of the cartilage anlage, and cartilage remaining between the metaphysis formed by the primary ossification center and the epiphysis formed by the secondary ossification center is called an epiphyseal plate, and until growth is completed, chondrocyte proliferation and endochondral ossification continue to progress.

Progenitor cells capable of producing bone and cartilage in the osteogenesis process are cells located in the intermediate stage of the differentiated bone cells or chondrocytes. The advantage of these cells is that unlike stem cells, which have a limitation in the control of a differentiation direction, the direction in which progenitor cells can differentiate into both cartilage and bone is determined and these cells can be mass-cultured due to their stronger proliferation capacity than differentiated cells. In addition, since such progenitor cells secrete growth factors, cytokines, and various proteins related to bone and cartilage production, studies on the use of active substances thereof are ongoing, but still remain in a research stage. In particular, there have been no studies on chicken osteochondroprogenitor cell secretions.

The inventors of the present invention confirmed that a cell culture solution obtained by mass-culturing osteochondroprogenitor cells derived from the long bone of a starter chick can promote osteogenic differentiation of human stem cells, and that, as a result of intensive research on whether a culture concentrate of chicken osteochondroprogenitor cells can be used in differentiation of stem cells into osteoblasts, in the case of inducing osteogenic differentiation of adipose tissue-derived stem cells, differentiation thereof into osteoblasts was promoted when co-treated with the culture concentrate of chicken osteochondroprogenitor cells, and thus completed the present invention.

Moreover, with the need for a new method for the productive use of starter male chicks, which are waste resources and more than 2.5 billion of which are killed annually worldwide using an inhumane method, a technique using cells of starter chicks can present a new direction in terms of the use of chickens.

DESCRIPTION OF EMBODIMENTS

Technical Problem

As a result of having conducted intensive studies to discover factors for promoting osteogenic differentiation efficiency of stem cells having multipotency or inducing chondrogenic differentiation of stem cells, the inventors of the present invention confirmed that a culture solution of osteochondroprogenitor cells derived from the long bone of a chicken enhanced the effect of existing bone cell inducers, thereby significantly enhancing the osteogenic differentiation efficiency of stem cells and inducing chondrogenic differentiation of stem cells, and thus completed the present invention.

Therefore, an object of the present invention is to provide a composition for promoting osteogenesis or inducing cartilage production, which includes, as an active ingredient, a culture solution of chicken bone marrow-derived osteochondroprogenitor cells, and a method of promoting osteogenic differentiation efficiency of stem cells by treatment with the culture solution.

Another object of the present invention is to provide a method of inducing chondrogenic differentiation of stem cells by treatment with the culture solution, and still another object of the present invention is to provide a pharmaceutical composition for preventing or treating cartilage damage or cartilage defects, which includes chondrocytes induced using the method.

However, technical problems to be solved by the present invention are not limited to the above-described technical problems, and other unmentioned technical problems will become apparent from the following description to those of ordinary skill in the art.

Technical Solution

According to an aspect of the present invention, there is provided a composition for promoting osteogenesis or inducing cartilage production, comprising a culture solution of chicken bone marrow-derived osteochondroprogenitor cells, as an active ingredient.

In one embodiment of the present invention, the chicken may be a starter chick.

In another embodiment of the present invention, the culture solution of chicken bone marrow-derived osteochondroprogenitor cells may be a culture concentrate.

In another embodiment of the present invention, the composition may further include an osteogenic differentiation inducer.

In another embodiment of the present invention, the composition may promote osteogenic differentiation of a stem cell.

In another embodiment of the present invention, the composition may induce chondrogenic differentiation of a stem cell.

In another embodiment of the present invention, the stem cell may be a mesenchymal stem cell.

In another embodiment of the present invention, the mesenchymal stem cell may be an adipose-derived mesenchymal stem cell.

The present invention also provides a method of promoting osteogenic differentiation efficiency of a stem cell, including treating the stem cell with a culture solution of chicken bone marrow-derived osteochondroprogenitor cells.

In one embodiment of the present invention, the chicken may be a starter chick.

In another embodiment of the present invention, the culture solution of chicken bone marrow-derived osteochondroprogenitor cells may be a culture concentrate.

In another embodiment of the present invention, the method may further include treating with an osteogenic differentiation inducer.

In another embodiment of the present invention, the stem cell may be a mesenchymal stem cell.

In another embodiment of the present invention, the mesenchymal stem cell may be an adipose-derived mesenchymal stem cell.

The present invention also provides a method of inducing chondrogenic differentiation of a stem cell, including treating the stem cell with a culture solution of chicken bone marrow-derived osteochondroprogenitor cells.

In one embodiment of the present invention, the chicken may be a starter chick.

In another embodiment of the present invention, the culture solution of chicken bone marrow-derived osteochondroprogenitor cells may be a culture concentrate.

In another embodiment of the present invention, the stem cell may be a mesenchymal stem cell.

In another embodiment of the present invention, the mesenchymal stem cell may be an adipose-derived mesenchymal stem cell.

In another embodiment of the present invention, the treatment of the stem cell with a culture solution of chicken bone marrow-derived osteochondroprogenitor cells may be performed by culturing stem cells in a medium containing the culture solution of chicken bone marrow-derived osteochondroprogenitor cells.

The present invention also provides a pharmaceutical composition for preventing or treating a bone disease, including, as an active ingredient, a culture solution or culture concentrate of chicken bone marrow-derived osteochondroprogenitor cells.

The present invention also provides a method of treating a bone disease, including administering, to an individual, a composition including, as an active ingredient, a culture solution or culture concentrate of chicken bone marrow-derived osteochondroprogenitor cells.

The present invention also provides a use of a culture solution or culture concentrate of chicken bone marrow-derived osteochondroprogenitor cells for treating a bone disease.

The present invention also provides a health functional food composition for preventing or alleviating a bone disease, including, as an active ingredient, a culture solution or culture concentrate of chicken bone marrow-derived osteochondroprogenitor cells.

The present invention also provides a pharmaceutical composition for preventing or treating cartilage damage or cartilage defects, including, as an active ingredient, a stem cell which is induced differentiation using the method, or a differentiated chondrocyte which is differentiated using the method.

The present invention also provides a method of treating chondrocyte damage or chondrocyte defects, including administering, to an individual, a composition including, as an active ingredient, a chondrocyte, the differentiation of which is induced using the method.

The present invention also provides a use of a chondrocyte, the differentiation of which is induced using the method, for treating cartilage damage or cartilage defects.

The present invention also provides a health functional food composition for preventing or alleviating cartilage damage or cartilage defects, including, as an active ingredient, a culture solution or culture concentrate of chicken bone marrow-derived osteochondroprogenitor cells.

Advantageous Effects of Invention

A composition for promoting osteogenesis or inducing cartilage production, according to the present invention, uses a culture solution of starter chick bone marrow-derived osteochondroprogenitor cells, and thus can more effectively differentiate stem cells into osteocytes, compared to when treated with an existing chemical-based differentiation inducer alone, which is used to induce osteogenic induction. Since starter chick bone marrow-derived osteochondroprogenitor cells can be mass-cultured due to their high proliferation potency and are high-quality osteochondroprogenitor cells that vigorously secrete various proteins that induce chondrogenic differentiation, the composition using a culture solution of starter chick bone marrow-derived osteochondroprogenitor cells that do not have a secondary ossification center can provide a chondrogenic differentiation inducer with high efficiency at low cost.

In addition, the present invention is economical due to the use of starter chicks, which are killed and discarded to acquire osteochondroprogenitor cells, and thus can present a novel method of using male chicks, which are considered as waste resources.

In addition, the composition of the present invention can be implemented in a variety of formulations, such as concentrates, powders, and gels, and can implement various treatment methods depending on the formulation, and is expected to be equally applicable to not only adipose tissue-derived stem cells but also various adult tissue-derived stem cells such as bone marrow, the periodontium, and umbilical cord blood.

Therefore, the composition of the present invention can be used as an agent for treating bone damage diseases requiring new bone formation or regeneration, such as osteoporosis, bone defect diseases, Paget's disease, femoral head avascular necrosis, and osteoarthritis, an adjuvant, and a health functional food for bone health, and is expected to be applicable as an agent for treating cartilage damage diseases requiring new cartilage formation or regeneration, such as degenerative arthritis, rheumatoid arthritis, fractures, damage to muscle tissue, plantar fasciitis, humerus epicondylitis, calcifying myositis, joint damage due to non-union or trauma of the fracture, an adjuvant, and a health functional food for joint health.

BEST MODE

Figure 1:
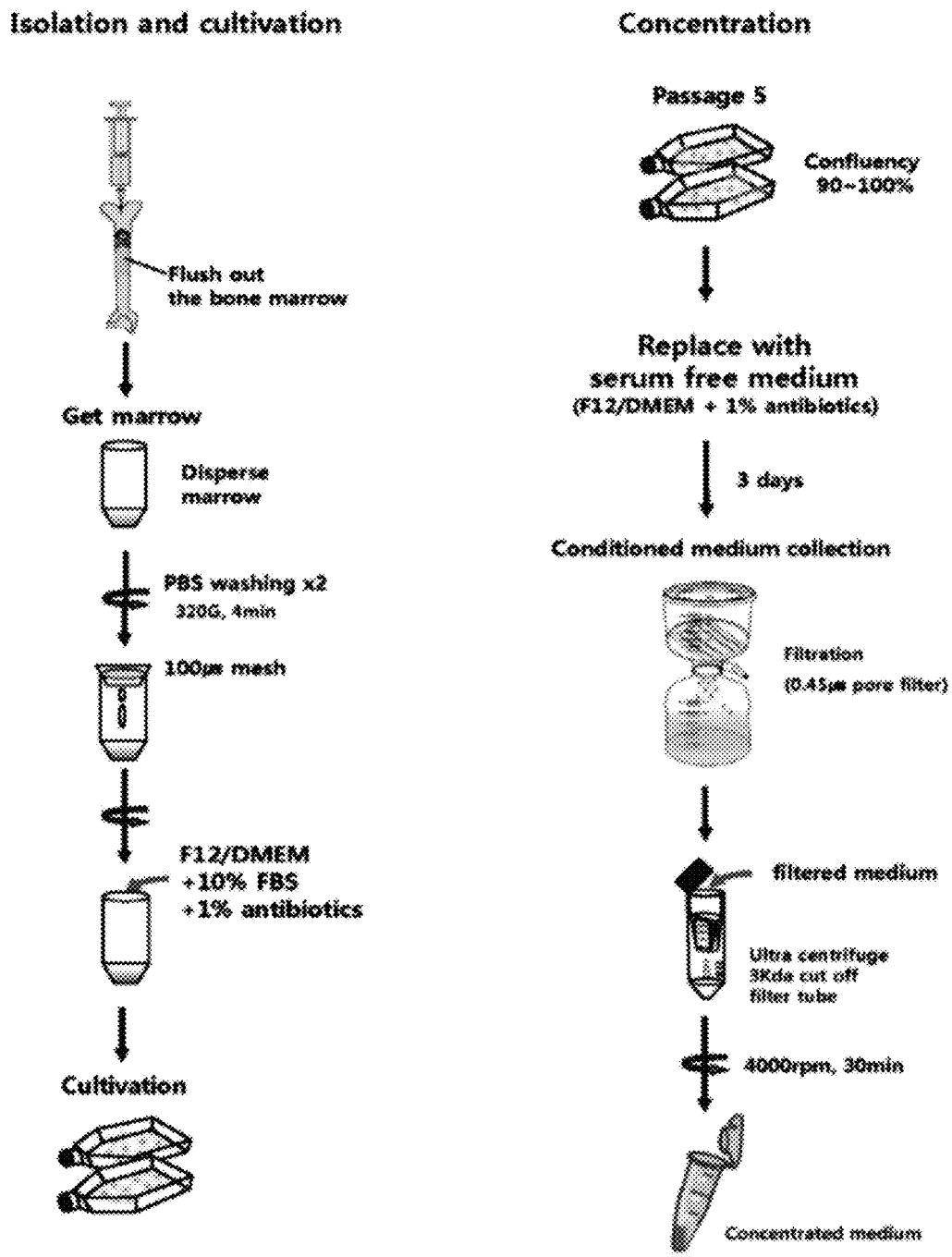
FIG. 1 is a schematic view illustrating a process of preparing a culture concentrate of chicken-derived osteochondroprogenitor cells.

As a result of having conducted intensive studies to discover factors for promoting osteogenic differentiation efficiency of stem cells having multipotency or inducing chondrogenic differentiation of stem cells, the inventors of the present invention confirmed that a culture solution of chicken long bone-derived osteochondroprogenitor cells enhanced the effect of existing osteogenic inducers, thereby significantly enhancing the osteogenic differentiation efficiency and differentiation rate of stem cells and inducing chondrogenic differentiation of stem cells, and thus completed the present invention.

Therefore, the present invention provides a composition for promoting osteogenic differentiation of a stem cell or inducing chondrogenic differentiation of a stem cell, the composition including, as an active ingredient, an osteochondroprogenitor cell culture solution, and a composition for promoting osteogenesis or inducing cartilage production.

In one embodiment of the present invention, the osteochondroprogenitor cell culture solution may be concentrated, and the "culture concentrate" may be prepared by filtering cells and cell debris from the osteochondroprogenitor cell culture solution using a vacuum filtration device and concentrating the filtered culture solution via a filter 2-fold to 1,000-fold, preferably 50-fold to 150-fold.

In the present invention, "osteochondroprogenitor cell" is a cell that has the ability to differentiate into bone and cartilage, but the fate of which has not yet been determined, is a cell in a phase between mesenchymal stem cells and osteoprogenitor cells that differentiate into osteocytes or chondroprogenitor cells that differentiate into chondrocytes, and is also present not only in bone marrow but also in bone tissue.

In the present invention, "stem cell" is a cell capable of differentiating into various cells constituting biological organs or tissues, and is not limited as long as it is a undifferentiated cell before differentiation which can be obtained from each tissue of an embryo, a fetus, and an adult, but preferably, may be a mesenchymal stem cell that can differentiate into an osteocyte. Stem cells differentiate into specific cells by differentiation stimulation (environment), and unlike differentiated cells in which cell division is stopped, stem cells proliferate (expand) due to their self-renewal ability to produce the same cells as themselves by cell division, and can also differentiate into other cells by different environments or different stimuli, and thus has plasticity in differentiation. Stem cells have pluripotency or multipotency.

In the present invention, "mesenchymal stem cell (MSC)" is not limited as long as it is a stem cell with multipotency which is capable of differentiating into an adipocyte, an osteocyte, a chondrocyte, a myocyte, a nerve cell, and a cardiomyocyte, and generally, mesodermal stem cells are identified through a morphological characteristic such as a spindle shape and the expression levels of basic cell surface markers CD73 (+), CD105 (+), CD34 (−), and CD45 (−).

According to one embodiment of the present invention, cells are recovered from the femur and calf bones of chicks within 4 days after hatching (see Example 1-1), and as a result of observation with an optical microscope, it was confirmed that the recovered cells had a morphological characteristic such as a small and cuboidal shape (see Example 1-3), and furthermore, as a result of analyzing the differentiation ability of the recovered cells, it was confirmed that the recovered cells differentiated into osteoblasts and chondrocytes, but not into adipocytes, from which it was confirmed that the recovered cells were osteochondroprogenitor cells (see Example 1-4).

Accordingly, according to one embodiment of the present invention, the osteochondroprogenitor cells are chicken bone marrow-derived osteochondroprogenitor cells, and more preferably, osteochondroprogenitor cells acquired from the matrix of a long bone (femur and calf bones) of a 4-day-week chick.

According to one embodiment of the present invention, by isolating single mesenchymal stem cells from human adipose tissue and analyzing cell phenotypes, the expression of CD105 (+), CD73 (+) CD31 (−), CD45 (−), HLA-DR (−), CD166 (+), CD34 (−), and CD90 (+) was confirmed, and by verifying the ability thereof to differentiate into osteoblasts, chondrocytes, and adipocytes, it was confirmed that the isolated cells were mesenchymal stem cells (See Example 2).

Accordingly, according to another embodiment of the present invention, stem cells inducing chondrogenic differentiation using a culture solution or culture concentration of chicken bone marrow-derived osteochondroprogenitor cells may be mesenchymal stem cells, the type of the mesenchymal stem cells is not particularly limited, and any mesenchymal stem cell may be used regardless of the origin thereof. The mesenchymal stem cells may be mesenchymal stem cells derived from various adult tissues obtained from a known source, for example, fat, bone marrow, tissue, an embryo, blood, bone marrow, the periodontium, and umbilical cord blood.

Thus, the inventors of the present invention experimentally confirmed that a culture concentrate, obtained by culturing chicken osteochondroprogenitor cells to prepare a serum-free culture solution thereof and concentrating the culture solution (see Examples 1-5 and 1-6), had an effect of promoting osteogenic differentiation efficiency of mesenchymal stem cells (see Examples 3-2 and 3-3).

Therefore, the present invention provides a method of promoting the osteogenic differentiation efficiency and/or differentiation rate of a stem cell by treating the stem cell with an osteochondroprogenitor cell culture solution or a culture concentrate obtained by concentrating the culture solution.

The present invention also provides a method of inducing chondrogenic differentiation of a stem cell by treating the stem cell with an osteochondroprogenitor cell culture solution or a culture concentrate obtained by concentrating the culture solution. The induction of the chondrogenic differentiation of a stem cell may be performed in vivo or in vitro. A method for the treatment of the stem cell with the culture solution or the culture concentrate is not particularly limited. That is, the method is any method of inducing chondrogenic differentiation of a stem cell by bringing the stem cell into contact with the culture solution or the culture concentrate for a certain period of time.

In one embodiment of the present invention, when the induction of chondrogenic differentiation of a stem cell is performed in vitro, stem cells may be cultured in a culture medium containing a culture solution of chicken bone marrow-derived osteochondroprogenitor cells or a culture concentrate obtained by concentrating the culture solution, but the present invention is not limited thereto.

The culture concentrate does not trigger the osteogenic differentiation of a stem cell, but can improve its efficiency when used in combination with an existing osteogenic differentiation inducer, which means that, when used in combination with the culture concentrate, bone damage diseases can be treated more effectively, compared to the case of using an osteogenic differentiation inducer alone as an agent for treating bone damage diseases. Therefore, a mixture of the osteochondroprogenitor cell culture solution of the present invention or the culture concentrate obtained by concentrating the culture solution and an osteogenic differentiation inducer may be applied to the treatment of diseases requiring bone regeneration or formation.

In addition, the osteochondroprogenitor cell culture solution of the present invention or the culture concentrate obtained by concentrating the culture solution may be applied to the treatment of diseases requiring cartilage regeneration or formation.

Therefore, the present invention provides a pharmaceutical composition for preventing or treating bone damage diseases, including, as an active ingredient, an osteochondroprogenitor cell culture solution or a culture concentrate obtained by concentrating the culture solution. The pharmaceutical composition may further include an osteogenic differentiation inducer, and the osteogenic differentiation inducer may be a known material for triggering osteogenic differentiation of a stem cell. In a specific embodiment of the present invention, as the osteogenic differentiation inducer, $10^{-8}$ M dexamethasone, 0.05 mM ascorbate-2-phosphate, and 10 mM β-glycerophosphate were added to a stem cell culture medium (DMEM medium supplemented with 10% fetal bovine serum and 1% antibiotic) (High abundance of CD271(+) multipotential stromal cells (MSCs) in intramedullary cavities of long bones. Cox G et al, Bone, 2012).

The present invention also provides a pharmaceutical composition for preventing or treating cartilage damage disease, including, as an active ingredient, an osteochondroprogenitor cell culture solution or a culture concentrate obtained by concentrating the culture solution.

The composition according to the present invention may be prepared into various formulations such as concentrates, powders, and gels, and various treatment methods may be implemented depending on the formulation.

The present invention also provides a composition for promoting differentiation of a stem cell into an osteocyte and a composition for promoting osteogenesis, the compositions using, as active ingredients, an osteochondroprogenitor cell culture solution or a culture concentrate obtained by concentrating the culture solution, and an osteogenic differentiation inducer.

In the present invention, "culture solution" refers to a solution remaining after culturing stem cells for a period of time in a liquid medium to support growth and survival of isolated stem cells in vitro, and then removing the cells, and contains proteins such as secreted growth factors and cytokines secreted from cells during a culture period and nutrients left over after consumption during cell culture. The medium includes all common mediums used in the art suitable for culturing adult stem cells, and medium and culture conditions may be selected according to the type of cells. The stem cell culture medium may be a cell culture minimum medium (CCMM) that generally includes a carbon source, a nitrogen source, and trace element components, and non-limiting examples thereof include Dulbecco's Modified Eagle's Medium (DMEM), Minimal Essential Medium (MEM), Basal Medium Eagle (BME), RPMI1640, F-10, F-12, αMinimal Essential Medium (αMEM), Glasgow's Minimal Essential Medium (GMEM), and Iscove's Modified Dulbecco's Medium (IMDM). In addition, the medium may further include an antibiotic such as penicillin, streptomycin, or gentamicin, and/or serum additives such as fetal bovine serum (FBS) and human serum albumin. In examples of the present invention, a DMEM medium containing 10% fetal calf serum and 1% antimicrobial agent was used as the stem cell culture medium.

In addition, in the present invention, "culture concentrate" means those obtained by collecting the culture solution using a method known in the art (e.g., centrifugation) and concentrating the collected culture solution. The concentrated culture solution may be cryopreserved, and as necessary, may be used after thawing and dilution to a desired concentration, and dried powder thereof may be used.

According to one embodiment of the present invention, the osteochondroprogenitor cell culture concentrate may be prepared by removing cells and cell debris from the osteochondroprogenitor cell culture solution using a vacuum filtration device and concentrating the filtered culture solution via a filter 2-fold to 1,000-fold, preferably 50-fold to 150-fold.

The composition according to the present invention may be prepared into various formulations such as concentrates, powders, and gels, and various treatment methods may be implemented depending on the formulation.

In the present invention, "bone damage disease" or "bone disease" refers to a disease that requires bone regeneration or formation in treatment thereof, and non-limiting examples thereof include osteoporosis, non-union fractures, osteonecrosis, osteomalacia, bone defect disease, Paget's disease, avascular necrosis of the femoral head, and osteoarthritis. Avascular necrosis of the femoral head is an intractable bone disease in which blood supply to the femoral head constituting hip joints is stopped due to trauma, drinking, taking steroids, and the like, resulting in bone destruction, and osteoporosis is a condition where the density of bones is significantly reduced compared to normal people and refers to a metabolic bone disease in which a quantitative reduction in components of the bone is a main lesion.

In the present invention, "cartilage damage disease" or "cartilage disease" refers to a disease that requires cartilage regeneration or formation in treatment thereof, refers to a disease occurring resulting from damage to cartilage, cartilage tissue and/or joint tissue (synovial membrane, articular cell, subchondral bone, or the like) due to a mechanical stimulus or an inflammatory reaction, and may be understood as encompassing "cartilage defect disease." Non-limiting examples thereof include degenerative arthritis, rheumatoid arthritis, fractures, damage to muscle tissue, plantar fasciitis, humerus epicondylitis, calcifying myositis, and joint damage due to non-union or trauma of the fracture.

In the present invention, the term "prevention" means any action that inhibits or delays the development, spread or recurrence of bone damage or bone-related diseases, and cartilage damage or cartilage-related diseases via administration of the composition of the present invention, and the term "treatment" means any action in which symptoms of the disease are improved or beneficially altered via administration of the composition of the present invention.

In the present invention, the term, "pharmaceutical composition" means a composition prepared for preventing or treating a disease, and may be formulated into various forms according to each general method. For example, the composition may be formulated into oral dosage forms such as powders, granules, tablets, capsules, suspensions, emulsions, and syrups, and may be formulated in the form of external preparations, suppositories, and sterile injectable solutions.

In addition, according to each formulation, the composition may be prepared by further including a pharmaceutically acceptable carrier known in the art, such as a buffer, preservative, a painless agent, a solubilizer, an isotonic agent, a stabilizer, a base, an excipient, and a lubricant.

Meanwhile, the pharmaceutical composition of the present invention may be administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the health condition of patients, the severity of disease, the activity of drugs, sensitivity to drugs, administration time, administration route, excretion rate, treatment period, and simultaneously used drugs, and other factors well known in the medical field.

Thus, according to the present invention, bone damage-related diseases or cartilage damage-related diseases may be prevented or treated by administering, to an individual, a composition including an osteochondroprogenitor cell culture solution or a culture concentrate obtained by concentrating the culture solution, and the bone damage- or bone-related diseases may be, preferably, one selected from the group consisting of osteoporosis, bone defect diseases, Paget's disease, femoral head avascular necrosis, and osteoarthritis, and the cartilage damage- or cartilage-related diseases may be, preferably, one selected from the group consisting of degenerative arthritis, rheumatoid arthritis, fractures, damage to muscle tissue, plantar fasciitis, humerus epicondylitis, calcifying myositis, and joint damage due to non-union or trauma of the fracture.

In the present invention, the term "individual" may be a mammal such as a rat, livestock, a mouse, or a human, specifically, a companion dog, a race horse, or a human in need of treatment for bone disease or cartilage disease, preferably human. The pharmaceutical composition of the present invention may be formulated in various forms for administration to an individual, and a representative example of the formulation for parenteral administration is an isotonic aqueous solution or suspension as a formulation for injection. Injectable formulations may be prepared according to techniques known in the art using suitable dispersing or wetting agents and suspending agents. For example, each component may be formulated for injection by dissolving each component in saline or buffer. In addition, oral dosage forms include, for example, ingestible tablets, buccal tablets, troches, capsules, elixirs, suspensions, syrups, wafers, and the like. These preparations include, in addition to the active ingredient, a diluent (e.g., lactose, dextrose, sucrose, mannitol, sorbitol, cellulose, and/or glycine), and a lubricant (e.g., silica, talc, stearic acid and magnesium or calcium salts thereof, and/or polyethylene glycol). Tablets may include a binder such as magnesium aluminum silicate, starch paste, gelatin, tragacanth, methyl cellulose, sodium carboxymethyl cellulose, and/or polyvinyl pyrrolidone, and in some cases, may include a disintegrating agent such as starch, agar, alginic acid or sodium salts thereof, an absorbent, a coloring agent, a flavoring agent, and/or a sweetening agent. The formulations may be prepared by general mixing, granulation, or coating.

In addition, the pharmaceutical composition of the present invention may further include an adjuvant such as a preservative, a hydrating agent, an emulsifying accelerator, a salt for the control of osmotic pressure, or a buffer, and other therapeutically effective materials, and may be formulated using a general method.

The pharmaceutical composition according to the present invention may be administered via various routes including oral, transdermal, subcutaneous, intravenous or intramuscular administration and the dosage of the active ingredient may be appropriately selected according to various factors such as administration route, the age, gender, body weight of a patient, and the severity of a disease. In addition, the composition of the present invention may be administered in combination with a known compound capable of enhancing a desired effect.

The pharmaceutical composition according to the present invention may be administered to humans and animals orally or parenterally via intravenous, subcutaneous, intranasal, or intraperitoneal administration. Oral administration also includes sublingual application. Parenteral administration includes injection and drip methods such as subcutaneous injection, intramuscular injection, and intravenous injection.

In the pharmaceutical composition of the present invention, a total effective amount of the culture solution or culture concentration of chicken bone marrow-derived osteochondroprogenitor cells may be administered as a single dose to a patient, and the pharmaceutical composition may be administered in a multiple dose by a fractionated treatment protocol for long-term administration. In the pharmaceutical composition of the present invention, the amount of the active ingredient may vary depending on the severity of disease, but the active ingredient may generally be repeatedly administered several times a day at an effective dose of 100 µg to 3,000 mg per a single dose for an adult. However, an effective amount of the culture solution or the culture concentrate to be administered to a patient may be determined by various factors such as not only administration route and the number of treatments, but also the age, body weight, health condition, and gender of a patient, the severity of disease, diet, and excretion rate. Thus, in consideration of the above factors, a suitable effective dosage level of the culture solution or the culture concentrate may be determined by one of ordinary skill in the art depending on a specific use as an agent for treating or preventing bone damage or bone-related diseases, and the formulation, administration route, and administration method of the pharmaceutical composition according to the present invention are not particularly limited as long as they exhibit the effect of the present invention.

In addition, the pharmaceutical composition of the present invention may further include a known osteogenic inducer or chondrogenic inducer, in addition to the active ingredient, i.e., the culture solution or culture concentrate of chicken bone marrow-derived osteochondroprogenitor cells, and may be used in combination with known other therapies for the treatment of these diseases.

The composition of the present invention including, as an active ingredient, a culture solution or culture concentrate of chicken bone marrow-derived osteochondroprogenitor cells may be used in various drugs, foods, beverages, and the like that are effective in preventing or alleviating bone-related diseases or cartilage-related diseases. Foods to which the composition of the present invention including, as an active ingredient, a culture solution or culture concentrate of chicken bone marrow-derived osteochondroprogenitor cells may be added may be, for example, various foods, beverages, gums, teas, vitamin complexes, health supplement foods, and the like, and may be used in the form of powders, granules, tablets, capsules, or beverages.

In addition, the composition of the present invention including, as an active ingredient, a culture solution or culture concentrate of chicken bone marrow-derived osteochondroprogenitor cells may be added to foods or beverages to prevent and alleviate bone-related diseases or cartilage-related diseases requiring bone regeneration or formation or cartilage regeneration or formation. In this regard, the amount of the compound in a food or a beverage may generally be in the range of 0.01 wt % to 15 wt % with respect to a total weight of the food, and a health beverage composition may be added in an amount of 0.02 g to 10 g, preferably 0.3 g to 1 g, with respect to 100 g.

A health functional food composition of the present invention may include the active ingredient as an essential ingredient at the indicated proportion, and may include additional ingredients such as sitologically acceptable food supplement additives, e.g., various flavoring agents or natural carbohydrates. Examples of the above-described natural carbohydrates include general sugars such as monosaccharides, e.g., glucose and fructose; disaccharides, e.g., maltose and sucrose; and polysaccharides such as dextrin and cyclodextrin, and sugar alcohols such as xylitol, sorbitol, and erythritol. As a flavoring agent other than the above-described flavoring agents, a natural flavoring agent (thaumatin and *stevia* extracts (e.g., rebaudioside A, glycyrrhizin, and the like) and a synthetic flavoring agent (saccharin, aspartame, and the like) may be used. The proportion of the natural carbohydrates may generally be in the range of about 1 g to about 20 g, preferably about 5 g to about 12 g, with respect to 100 ml of the health functional food of the present invention. In addition to the above-listed ingredients, the health functional food of the present invention may include various nutritional supplements, vitamins, minerals (electrolytes), flavors such as synthetic flavors and natural flavors, colorants and enhancers (cheese, chocolates, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. In addition, the health functional food of the present invention may include flesh for the preparation of natural fruit juice, fruit juice beverages, and vegetable beverages. These ingredients may be used alone or a combination thereof may be used. The proportion of these additives is not very important, but the amounts of the additives generally range from 0 part by weight to about 20 parts by weight with respect to 100 parts by weight of the composition of the present invention.

Hereinafter, exemplary examples will be described to aid in understanding of the present invention. However, the following examples are provided only to facilitate the understanding of the present invention and are not intended to limit the scope of the present invention.

MODE OF INVENTION

Example 1. Isolation and Culture of Osteochondroprogenitor Cells in Bone Marrow and Preparation of Culture Concentrate of Cells 1-1. Recovery of Progenitor Cells Capable of Differentiating from Hyaline Cartilage and Bone Marrow into Bone and Cartilage in Long Bone of Starter Chickens Femurs and tibias were recovered from both legs of chicks within 4 days after hatching and washed twice. After completely removing the muscles and tendons attached to the bones, the bones were again washed twice. For all cleaning procedures, phosphate-buffered saline (PBS) containing 1% antibiotics and antibacterial agents was used. Then, the cured parts of both sides of the bone were removed using surgical scissors, and a hole was made with an 18 gauge (G) needle, PBS with 1% antibiotic and 2% fetal bovine serum (FBS) was added to a 3 ml medical syringe with an attached 18 G needle and the syringe was pushed into the hole at the end of the bone to recover the matrix in the bone, and this process was repeated three times in both directions. The femur bone was recovered using an 18 G needle and the tibia was recovered using a 20 G needle. The matrix recovered from a total of 4 bones per animal was collected in a 14 ml round bottom tube, and the tissue was homogenized by passing 10 times with a syringe used for recovery. A 50 μm conical tube was put on a 100 μm pore mesh, and the homogenized matrix was filtered to remove bone chips or flesh that had introduced at the time of recovery. The tube was filled with PBS and centrifuged at 320 G for 4 minutes using a centrifuge to obtain a cell pellet, which is a cell mass precipitated at the bottom of the tube. Subsequently, the supernatant was removed, 5 ml of a basal medium (F12/DMEM) was added, and the cell pellet was released to make single cells.

1-2. Culture of Chicken Osteochondroprogenitor Cells

The cells recovered in Example 1-1 were placed at a density of $3\times10^6$ cells per 1 cm$^2$ of a culture vessel in an F12/DMEM medium supplemented with 3.151 g/L of D-glucose, 365 mg/L (2.5 mM) of L-glutamine, 55 mg/L (0.5 mM) of sodium pyruvate, 10% FBS, and 1% antibiotic-antibacterial agent, and incubated in a 5% $CO_2$ incubator under conditions of about 90% humidity and a temperature of 37° C. For subculture, the culture solution was removed when reaching a confluency of about 80-90%, followed by washing twice with cold PBS. After treating with 0.25% Trypsin-EDTA for 2 minutes, the cell suspension was recovered and centrifuged at 320 G for 4 minutes, and then the number of cells was measured and cell viability was examined, followed by again subculturing three times.

1-3. Characterization of Chicken Osteochondroprogenitor Cells

Figure 2A:
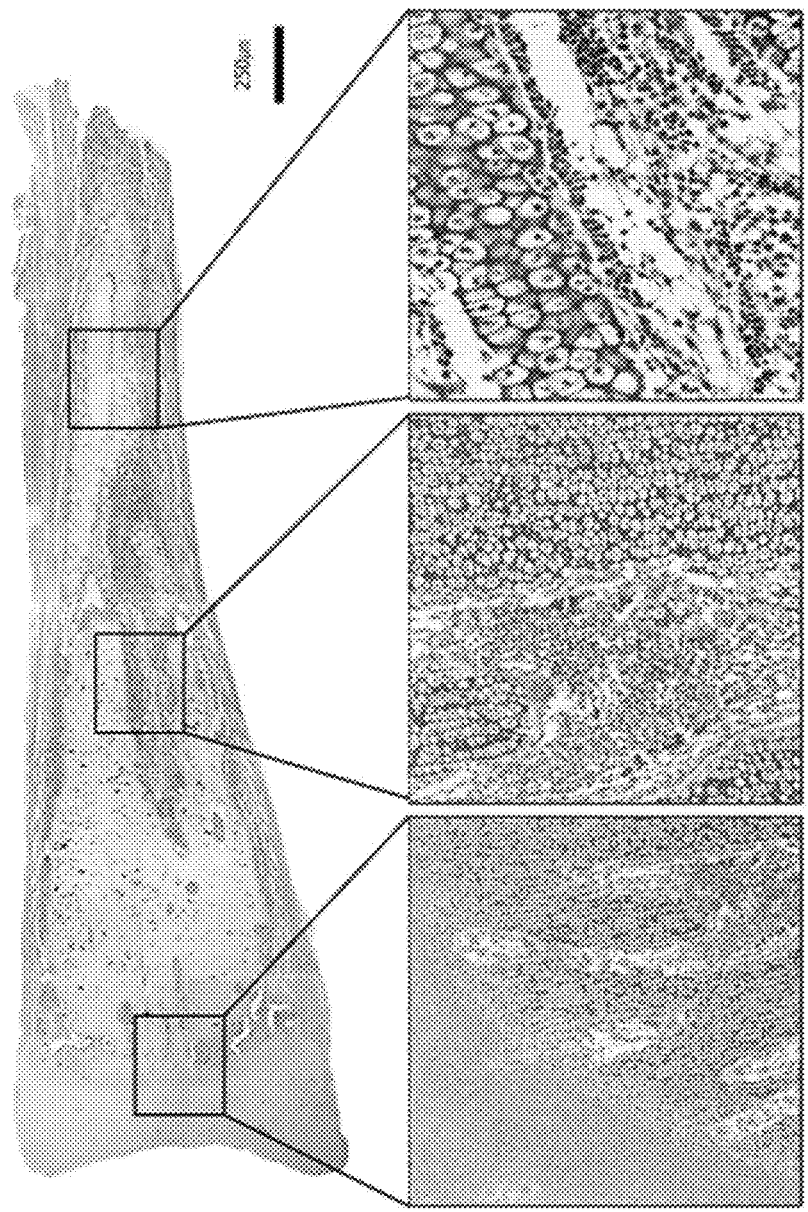
FIG. 2A illustrates a stained state of the long bone of a 4-day-old chick.

To analyze the morphological condition inside the long bone of a starter chick, histological staining was performed by hematoxylin-eosin staining. The long bone of a 4-day-old chick was immersed in a 4% paraformaldehyde fixative and fixed at room temperature for 24 hours. After washing, the fixed tissue was subjected to decalcification, clearing, and dehydration, and then embedded in paraffin. The tissue was sectioned to a thickness of 6 μm, and then placed on a heating block at 60° C. for 45 minutes to be deparaffinized, sequentially followed by washing three times with xylene for 5 minutes, three times with 100% ethanol for 5 minutes, twice with 95% ethanol for 2 minutes, twice with 70% ethanol for 2 minutes, and twice with distilled water for 2 minutes. After completion of the hydration process, the tissue sections were sequentially subjected to treatment with a 1% hematoxylin solution for 30 seconds, washing with distilled water, treatment with 0.25% hydrogen chloride for 1 second, washing with distilled water, and lithium carbonate coloring, thereby staining the nuclei. The cytoplasm was stained with eosin for 2 seconds, followed by dehydration, clearing, and mounting, and then observed using a microscope. As a result, as shown in FIG. 2A, it was confirmed that the long bone of a 4-day-old chick is filled with various stages of chondrocytes having a total area of 60% or more, and the epiphysis was maintained in a hyaline cartilage state in which a secondary ossification center had not yet been produced.

Subsequently, the morphology of the cells recovered and cultured through Examples 1-1 and 1-2 was photographed and confirmed using an optical microscope.

Figure 2B:
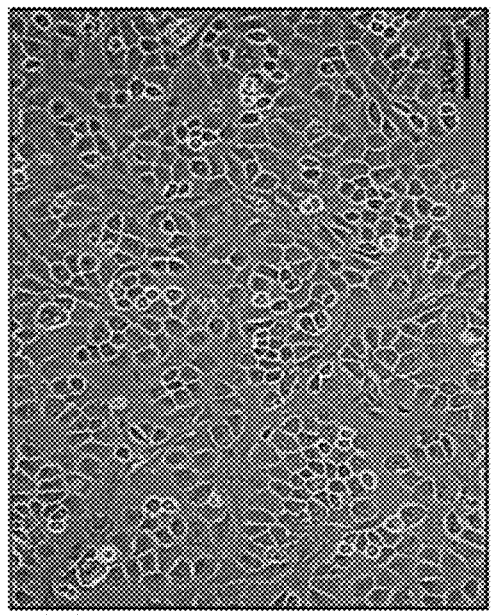
FIG. 2B illustrates the results of confirming the morphology of cells having been recovered from the long bone of a 4-day-old chick and cultured.
Figure 2B:
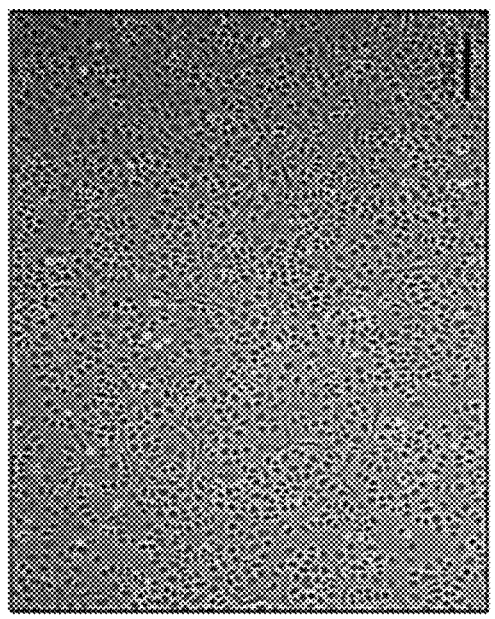

As a result, as shown in FIG. 2B, it was confirmed that the osteochondroprogenitor cells had a small and cuboidal shape, unlike mesenchymal stem cells, which are generally spindle-shaped.

Subsequently, the cells recovered in Example 1-1 were subjected to a fifth passage by the method of Example 1-2, followed by analysis of the gene expression levels of Sox9, Collagen type I, Collagen type II, and Runx2, and the protein expression levels of Sox9, Collagen type I, and Collagen type II, which are osteochondroprogenitor cell-related transcription factors.

Figure 2C:
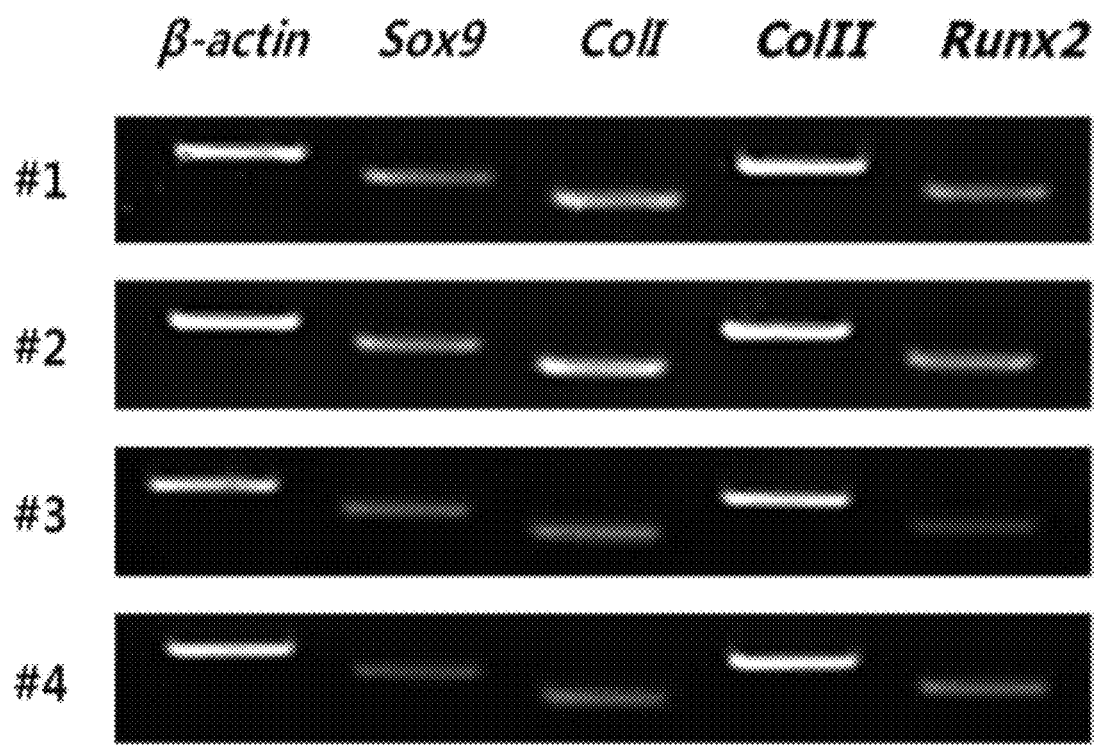
FIG. 2C illustrates the results of confirming the expression of genes related to bone and cartilage progenitor cells in cells having been recovered from the long bone of a 4-day-old chick and cultured.

Specifically, for the gene expression analysis, RNA was extracted by a phenol-chloroform extraction method using a TRIzol reagent, and reverse transcription-polymerase chain reaction (RT-PCR) was performed to synthesize cDNA, and then PCR was performed using primers specific to each gene using Sox9, Collagen type I, Collagen type II, Runx2, and β-actin genes, which are antigenic genes, as control genes. The information on primers used is shown in Table 1 below, and analysis results of the PCR product by electrophoresis on a 1% agarose gel are shown in FIG. 2C.

TABLE 1

| gene | SEQ ID NO: | Primer base sequence |
|---|---|---|
| β-actin | 1 | 5'-ATGAAGCCCAGAGCAAAAGA-3' |
|  | 2 | 5'-GGGGTGTTGAAGGTCTCAAA-3' |
| Sox9 | 3 | 5'-GCTTTCTCGCATGAATCTCC-3' |
|  | 4 | 5'-TTGGGGAAGGTGTTCTCTTG-3' |
| Collagen typeI | 5 | 5'-CAAACCAGGCGAAAGGGGTC-3' |
|  | 6 | 5'-AATGGACCACGGCTTCCAA-3' |
| Collagen typeII | 7 | 5'-AAGATGTTGTAGGACCCCGA-3' |
|  | 8 | 5'-CATCTGCGCCGCAAAGTTTC-3' |
| Runx2 | 9 | 5'-CAGACCAGCAGCACTCCATA-3' |
|  | 10 | 5'-TTGGGCAAGTTTGGGTTTAG-3' |

In addition, to analyze the protein expression level, the cells were fixed with 4% paraformaldehyde for 10 minutes, washed 3 times with PBS, and blocked with 1% BSA and a 10% goat serum solution. Each protein was treated with primary antibodies to cause a reaction at 4° C. for 18 hours, and then washed twice with PBS and treated with secondary antibodies (manufactured by Santa Cruz Biotechnology) fluorescently labeled for the primary antibodies to cause a reaction at room temperature for 1 hour. After washing twice with PBS, the nuclei were stained with 4',6-diamidine-2'-phenylindole (Dapi) for 1 minute. After mounting with a mounting solution, whether expression occurred was analyzed using a fluorescence microscope, and the results thereof are shown in FIG. 2D.

Figure 2D:
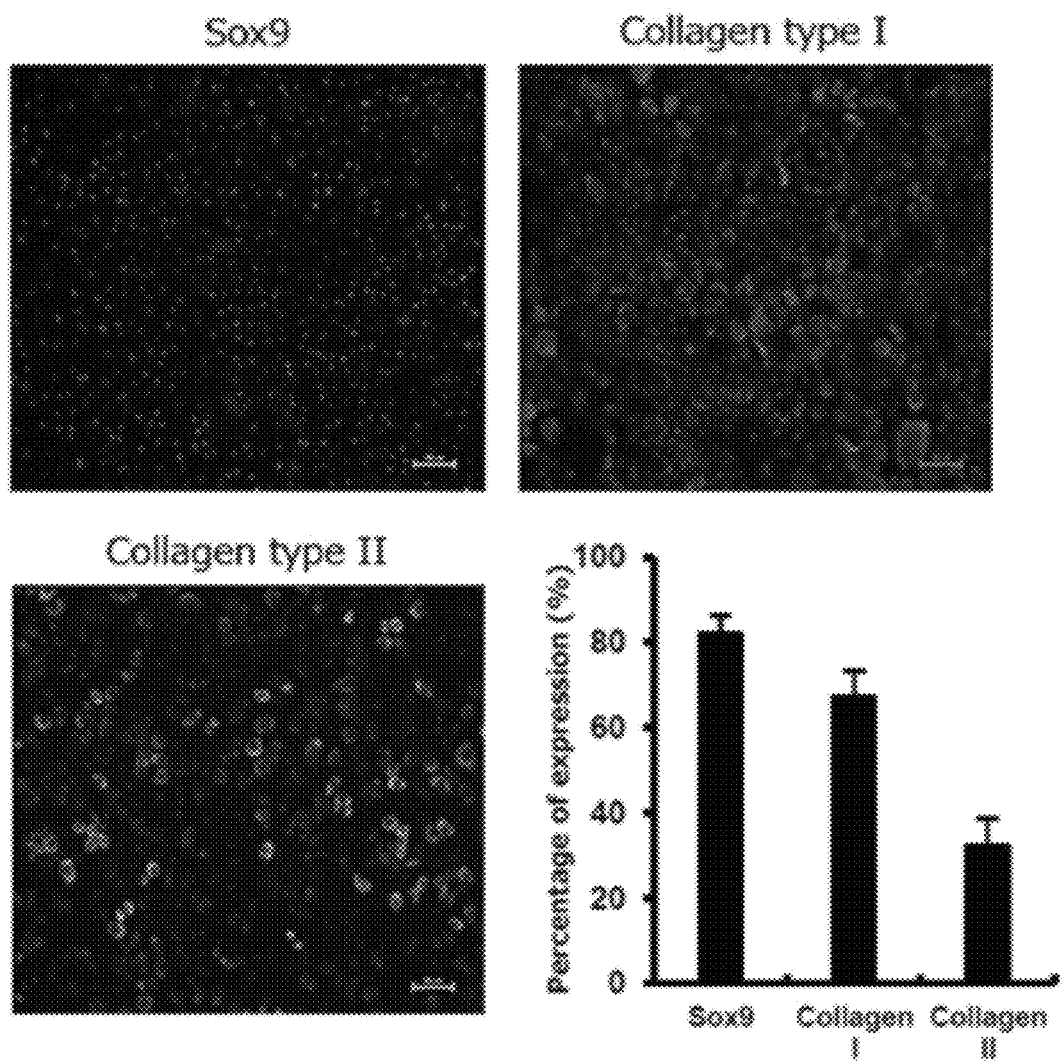
FIG. 2D illustrates the results of confirming the expression of proteins related to bone and cartilage progenitor cells in cells having been recovered from the long bone of a 4-day-old chick and cultured.

As a result, as shown in FIGS. 2C and 2D, it was confirmed that characteristic genes of osteochondroprogenitor cells, bone progenitor cells, or cartilage progenitor cells were expressed in the cultured cells, and specific proteins Sox9, Collagen type I, and Collagen type II were expressed.

1-4. Verification of Differentiation Capacity of Chicken Osteochondroprogenitor Cells To analyze whether the cells recovered and cultured according to Examples 1-1 and 1-2 are osteochondroprogenitor cells with multipotency, osteogenic differentiation, adipogenic differentiation, and chondrogenic differentiation were induced.

The osteogenic differentiation was induced for 21 days while replacing a low glucose DMEM culture medium supplemented with $10^{-7}$ M dexamethasone, 0.05 mM ascorbate-2-phosphate, 10 mM β-glycerophosphate, 10% FBS, and 1% antibiotic once every 3 days. After differentiation induction, Alizarin Red S (ARS, manufactured by Sigma) staining was performed to analyze whether the osteogenic differentiation occurred.

The adipogenic differentiation was induced for 21 days while replacing a low glucose DMEM culture medium supplemented with $10^{-6}$ M dexamethasone, 0.5 mM 3-siobutyl1-methylxanthine (IBMX), 0.1 mM indomethacin, 10 μg/ml bovine insulin (PH 2.5), 10% FBS, 1% antibiotic once every 3 days. After differentiation induction, Oil Red O (ORO, manufactured by Sigma) staining was performed to analyze whether the adipogenic differentiation occurred.

The chondrogenic differentiation was induced for 21 days while replacing a DMEM/F12 culture medium supplemented with 10 ng/ml of TGF-β1, $10^{-7}$ M dexamethasone, 1% ITS, 1.25 mg/ml of BSA, 5 mg/ml of linoleic acid, 50 mg/ml of ascorbic acid-2-phosphate, 40 μg/ml of L-proline, 10% FBS, and 1% antibiotic once every 3 days. After differentiation induction, Alcian blue staining was performed to analyze whether the chondrogenic differentiation occurred.

Figure 2E:
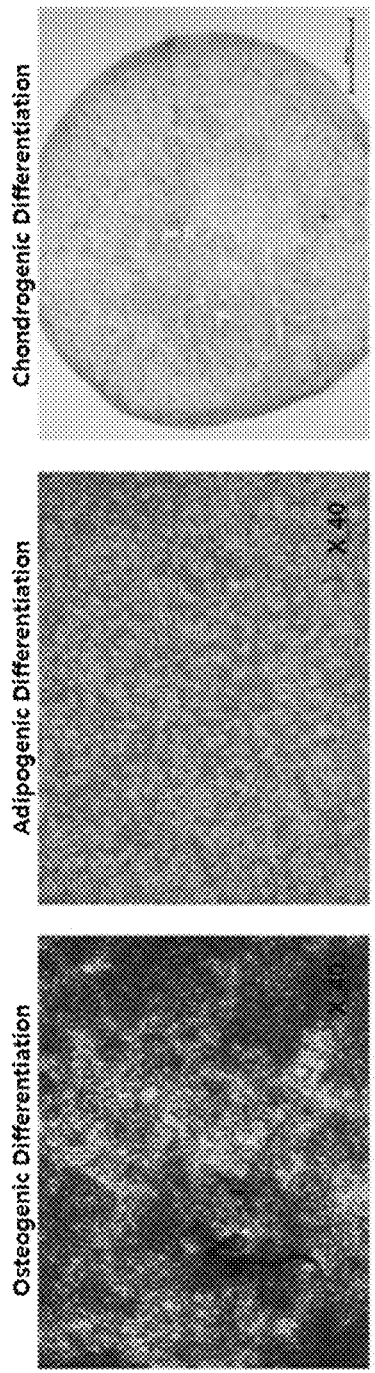
FIG. 2E illustrates the results of confirming that, by verifying the multipotency of cells having been recovered from the long bone of a 4-day-old chick and cultured, the cells were osteochondroprogenitor cells.

As a result, as illustrated in FIG. 2E, it was confirmed that the chicken cells recovered using the method of Example 1-1 differentiated into osteocytes and chondrocytes, but did not differentiate into adipocytes. The results mean that the chicken cells recovered using the method of Example 1-1 are osteochondroprogenitor cells capable of differentiating into bone and cartilage.

1-5. Preparation of Serum-Free Culture Solution of Chicken Osteochondroprogenitor Cells When the confluency of cells obtained by subjecting the chicken cells recovered using the method of Example 1-1 to the fifth passage using the method of Example 1-2 reached about 90-100%, the culture solution was removed, followed by washing three times with cold PBS. The cells were placed in an F12/DMEM medium supplemented with 3.151 g/L of D-glucose, 657 mg/L (4.5 mM) of L-glutamine, 110 mg/L (1 mM) of sodium pyruvate, and 1% antibiotic-antibacterial agent, and then incubated in a 5% $CO_2$ incubator under conditions of about 90% humidity and a temperature of 37° C., thereby preparing a serum-free culture solution of osteochondroprogenitor cells.

1-6. Preparation of Culture Concentrate of Chicken Osteochondroprogenitor Cells

To prepare a culture concentrate of chicken osteochondroprogenitor cells, as illustrated in FIG. 1, the culture solution prepared according to Example 1-5 was recovered and filtered using a disposable vacuum filtration device (0.45 μm pore size, manufactured by Corning) to remove residual cells and cell debris. The filtered culture solution was concentrated 100-fold using an ultra-centrifugal filter (3 Kda cut off, manufactured by Amicon). The concentrated culture solution had a protein concentration of 2-3 mg/ml, and was dispensed at a dose of 500 μg and stored at −20° C. In the following examples, the culture concentrate was slowly dissolved in a 4° C. refrigerator and used.

Figure 3A:
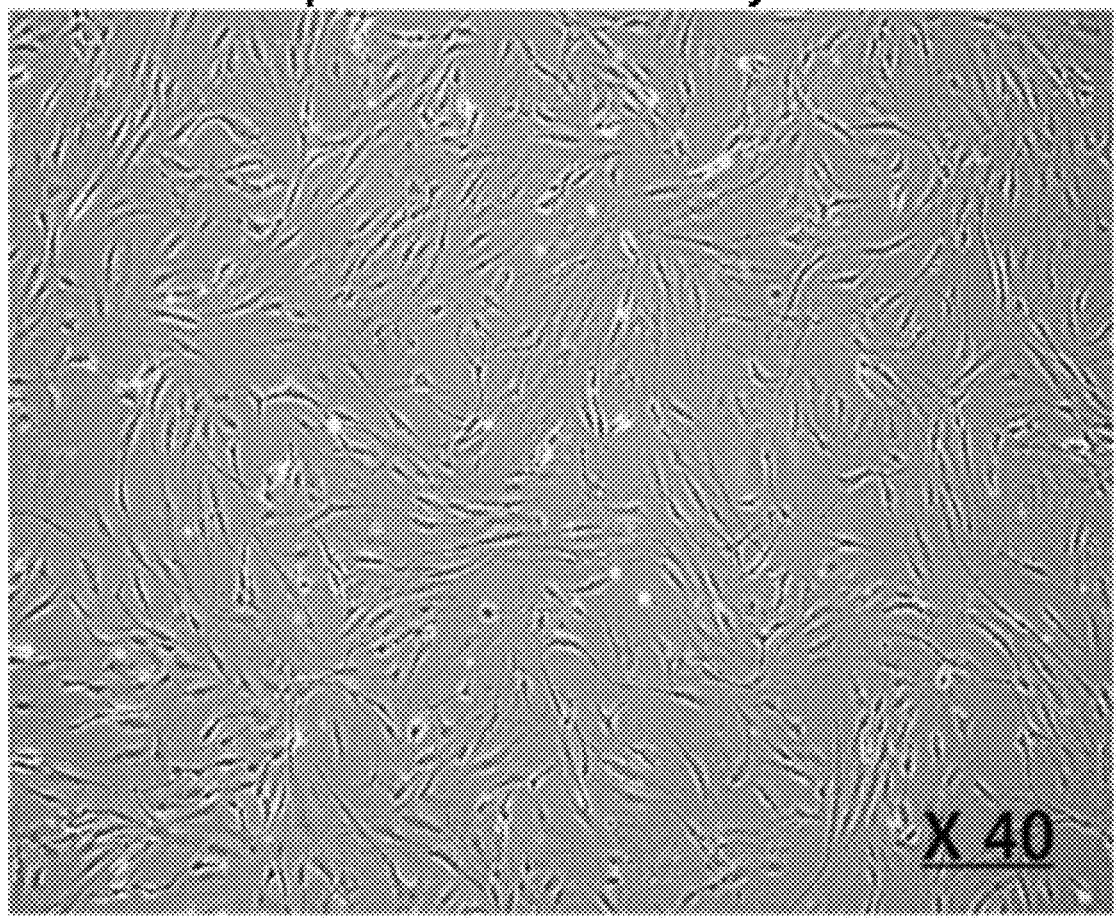
FIG. 3A is an image showing human adipose-derived mesenchymal stem cells acquired according to an embodiment of the present invention.

Example 2. Acquisition and Characterization of Human Adipose Tissue-Derived Mesenchymal Stem Cells 2-1. Isolation and Culture of Single Mesenchymal Stem Cells from Adipose Tissue The collected visceral adipose tissue (omental adipose tissue) was washed three times with cold PBS containing 1% antibiotic-antibacterial agent. The blood vessels, coagulated blood, and connective tissue attached to the washed tissue were removed with forceps and surgical scissors and again washed twice. The tissue was placed in a 100 ml glass bottle and cut into pieces to a size of 5 $mm^2$ or less using surgical scissors, and then a DMEM medium to which 0.1% collagenase type I (manufactured by Sigma-Aldrich) was added was added at a volume that was twice the volume of the tissue and slowly stirred in a 37° C. incubator for 30 minutes so that an enzymatic reaction sufficiently occurred. After the enzymatic reaction, the medium was collected in a tube and stored in ice, and a new enzyme medium was added and the above process was repeated once. The media recovered in the first and second processes were combined, filtered via a 100 μm pore mesh, and then centrifuged at 320 G for 4 minutes. The pure fat layer was removed, the mononuclear layer was collected, washed twice, and then immersed in an erythrocyte hemolysis solution (manufactured by Gibco BRL) to remove red blood cells to cause a reaction at room temperature for 10 minutes. After washing twice again, the number of cells and cell viability were measured, and the cells were dispensed at a density of $1\times10^5$ cells/area ($cm^2$) in an F12/DMEM medium supplemented with 5 ng/ml of human recombinant basic fibroblast growth factor (hrbFGF, manufactured by Gibco BRL), 10% FBS, and 1% antibiotic, and incubated in a 5% $CO_2$ incubator under conditions of about 90% humidity and a temperature of 37° C. After dispensing the cells, the medium was replaced every three days, and sub-culture was performed when the confluency reached 80-90%. After passage 5, the morphology of the cells was photographed and characterized, and then used for the experiment. FIG. 3A illustrates the results of confirming the morphology of the photographed cells after passage 5.

2-2. Cell Phenotyping

To verify the characteristics of the mesenchymal stem cells isolated and cultured in Example 2-1, FACSCalibur (manufactured by B&D Bioscience, CellQuest™ Pro) was used to confirm whether CD105, CD73, CD31, CD45, HLA-DR, CD166, CD34, and CD90, which are mesenchymal stem cell markers, were expressed.

Figure 3B:
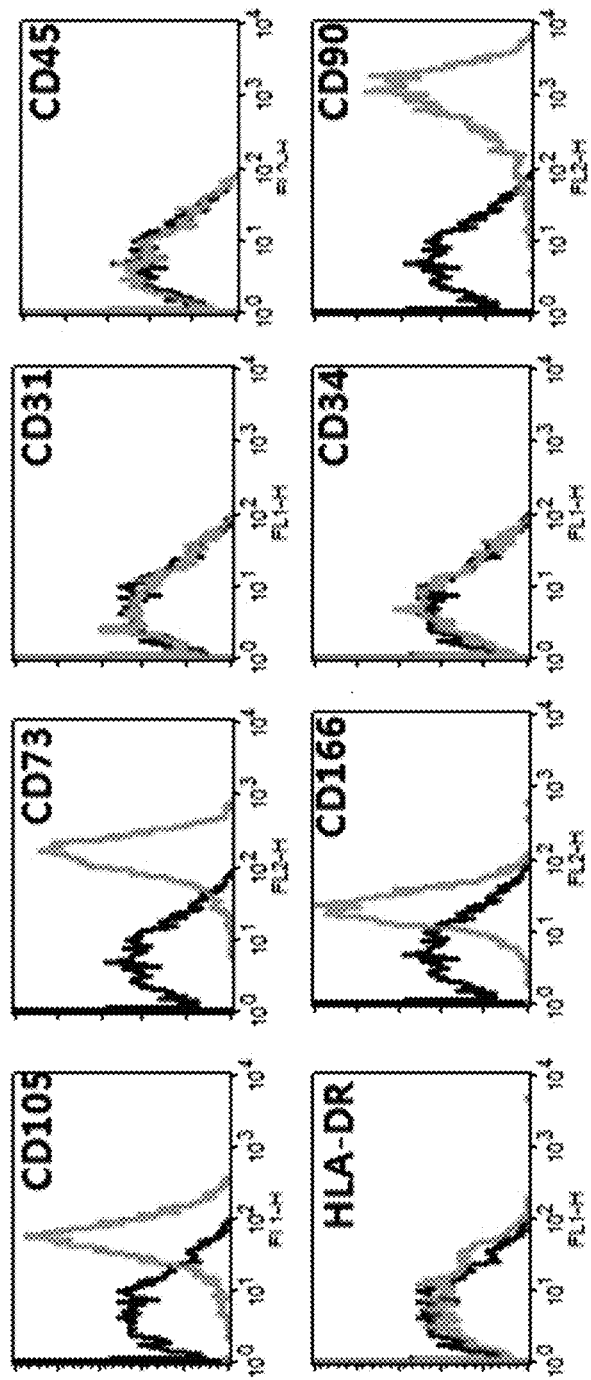
FIG. 3B illustrates the results of confirming that, by analyzing the protein expression of cells acquired according to an embodiment of the present invention, the acquired cells were mesenchymal stem cells.

As a result, as shown in FIG. 3B, CD31 (vascular endothelial cells), CD34 (hematopoietic stem cells), CD45 (hematopoietic cells), and MHC class II (leukocyte antigen class II) antigens were analyzed as negative, and CD105, CD73, CD166, and CD90 antigens were analyzed as positive, and it was confirmed that the isolated cells expressed all of the mesenchymal stem cell markers.

2-3. Multipotency Analysis

To analyze whether the mesenchymal stem cells isolated and cultured in Example 2-1 have multipotency, osteogenic differentiation, adipogenic differentiation, and chondrogenic differentiation were induced.

The osteogenic differentiation was induced for 21 days while replacing a low glucose DMEM culture medium supplemented with $10^{-7}$ M dexamethasone, 0.05 mM ascorbate-2-phosphate, 10 mM β-glycerophosphate, 10% FBS, and 1% antibiotic once every 3 days. After differentiation induction, Alizarin Red S (ARS, manufactured by Sigma) staining was performed to analyze whether the osteogenic differentiation occurred.

The adipogenic differentiation was induced for 21 days while replacing a low glucose DMEM culture medium supplemented with $10^{-6}$ M dexamethasone, 0.5 mM 3-siobutyl1-methylxanthine (IBMX), 0.1 mM indomethacin, 10 μg/ml bovine insulin (PH 2.5), 10% FBS, 1% antibiotic once every 3 days. After differentiation induction, Oil Red O (ORO, manufactured by Sigma) staining was performed to analyze whether the adipogenic differentiation occurred.

The chondrogenic differentiation was induced for 21 days while replacing a DMEM/F12 culture medium supplemented with 10 ng/ml of TGF-β1, $10^{-7}$ M dexamethasone, 1% ITS, 1.25 mg/ml of BSA, 5 μg/ml of linoleic acid, 50 μg/ml of ascorbic acid-2-phosphate, 40 μg/ml of L-proline, 10% FBS, and 1% antibiotic once every 3 days. After differentiation induction, Alcian blue staining was performed to analyze whether the chondrogenic differentiation occurred.

Figure 3C:
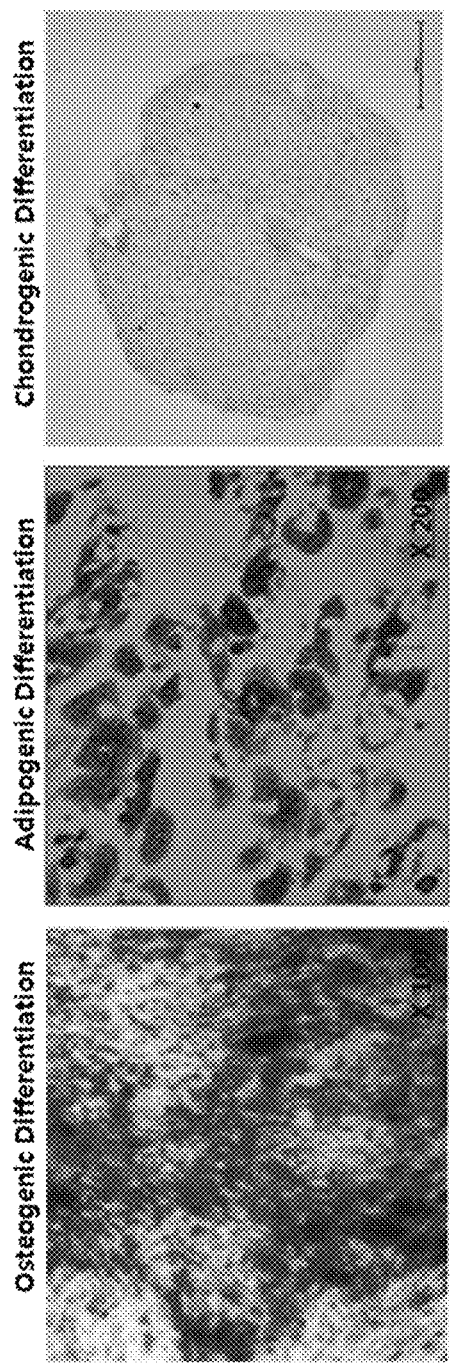
FIG. 3C illustrates the results of confirming that, by verifying the multipotency of cells acquired according to an embodiment of the present invention, the acquired cells were mesenchymal stem cells.

As a result, as illustrated in FIG. 3C, it was confirmed that the mesenchymal stem cells isolated and cultured in Example 2-1 had multipotency which enables osteogenic, adipogenic, and chondrogenic differentiation.

Example 3. Test for Promotion of Osteogenic Differentiation of Human Adipose Tissue-Derived Mesenchymal Stem Cells In order to confirm that the culture concentrate prepared according to Example 1 promotes osteogenic differentiation of of the human adipose tissue-derived mesenchymal stem cells acquired in Example 2, the culture concentrate was added to the medium at a concentration of 200 ug/mL. Particularly, a DMEM medium supplemented with 10% FBS and 1% antibiotic was used as a stem cell culture medium, and a DMEM medium supplemented with $10^{-7}$ M dexamethasone, 0.05 mM ascorbate-2-phosphate, 10 mM β-glycerophosphate, 10% FBS, and 1% antibiotic was used as the osteogenic induction differentiation medium.

3-1. Osteogenic Differentiation Induction

The human adipose tissue-derived mesenchymal stem cells at 5 passages were seeded into a 6-well culture plate (manufactured by SPL) at a density of $2\times10^5$ cells/well, and then when reaching a confluency of about 90%, osteogenic differentiation was induced. The osteogenic differentiation was performed as follows by culture in four media, respectively for 14 days or 21 days, and the medium was replaced once every three days: 1) a DMEM medium (stem cell culture medium, control) free of a differentiation inducer and supplemented with 10% FBS and 1% antibiotic; 2) an osteogenic induction differentiation medium (group treated with osteogenic differentiation inducer alone); 3) an osteogenic induction differentiation medium treated with the culture concentrate prepared according to Example 1-6 (group co-treated with osteogenic differentiation inducer and the culture concentrate; and 4) a medium treated with the culture concentrate culture alone (group treated with cell culture concentrate alone).

3-2. Confirmation of Osteogenic Differentiation Efficiency Through Alizarin Red S Staining Osteogenic differentiation was induced using the method of Example 3-1 according to time, and then Alizarin Red S (ARS, manufactured by Sigma) was performed. ARS has a property of binding to metal ions, and thus can be used to determine whether osteogenic differentiation is caused through staining a calcium precipitate (mineralization) secreted from cells. The cell sample at the time of completion of differentiation was treated with 4% paraformaldehyde (PFA) at room temperature for 1 hour to fix the cells. The fixed cells were washed twice with D.W and treated with a 1% ARS staining solution at room temperature for 15 minutes. At this time, the ARS solution was prepared by diluting 1% ARS with D.W of pH 4.5, followed by stirring using a magnetic bar for 18 hours and filtering, and used. The stained cells were washed five times with D.W and then photographed after confirming ARS staining on an optical microscope.

Figure 4:
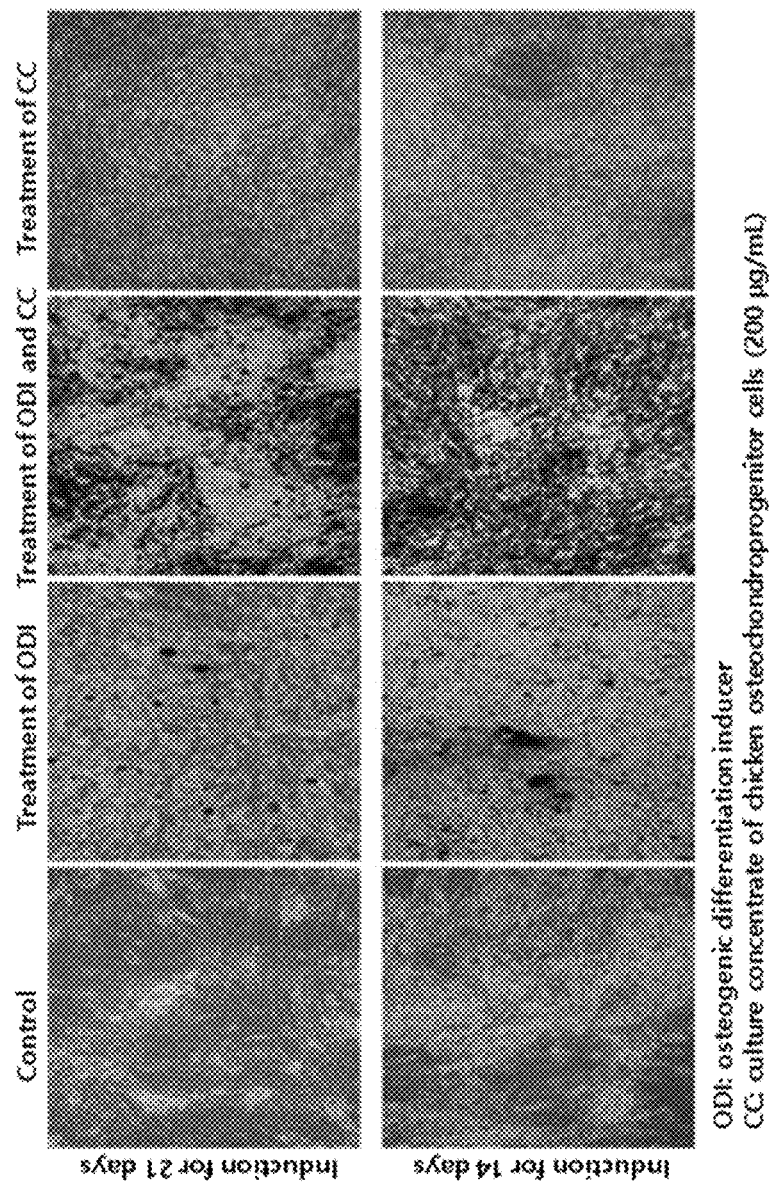
FIG. 4 illustrates the results of confirming the degree of osteogenic differentiation of mesenchymal stem cells cultured for 14 days or 21 days in a stem cell culture medium, an osteogenic induction differentiation medium, an osteogenic induction differentiation medium mixed with a culture concentrate of chicken-derived osteochondroprogenitor cells, or a stem cell culture medium mixed with a culture concentrate of chicken-derived osteochondroprogenitor cells.

As a result, as illustrated in FIG. 4, it was confirmed that, compared to the group treated with an osteogenic differentiation inducer alone, osteogenic differentiation was effectively increased on day 14 in the group co-treated with an osteogenic differentiation inducer and a cell culture concentrate, and that the osteogenic differentiation effect was maximized on day 21. In contrast, it was confirmed that differentiation was not induced in the control cultured in a basal culture medium and the group treated with a cell culture concentrate alone.

Next, to re-confirm whether the culture concentrate promotes the osteogenic differentiation efficiency and differentiation rate of stem cells, the osteogenic differentiation of which has been induced, the same experiment as the above experiment was performed on adipose tissue-derived mesenchymal stem cells of three people.

Figure 5:
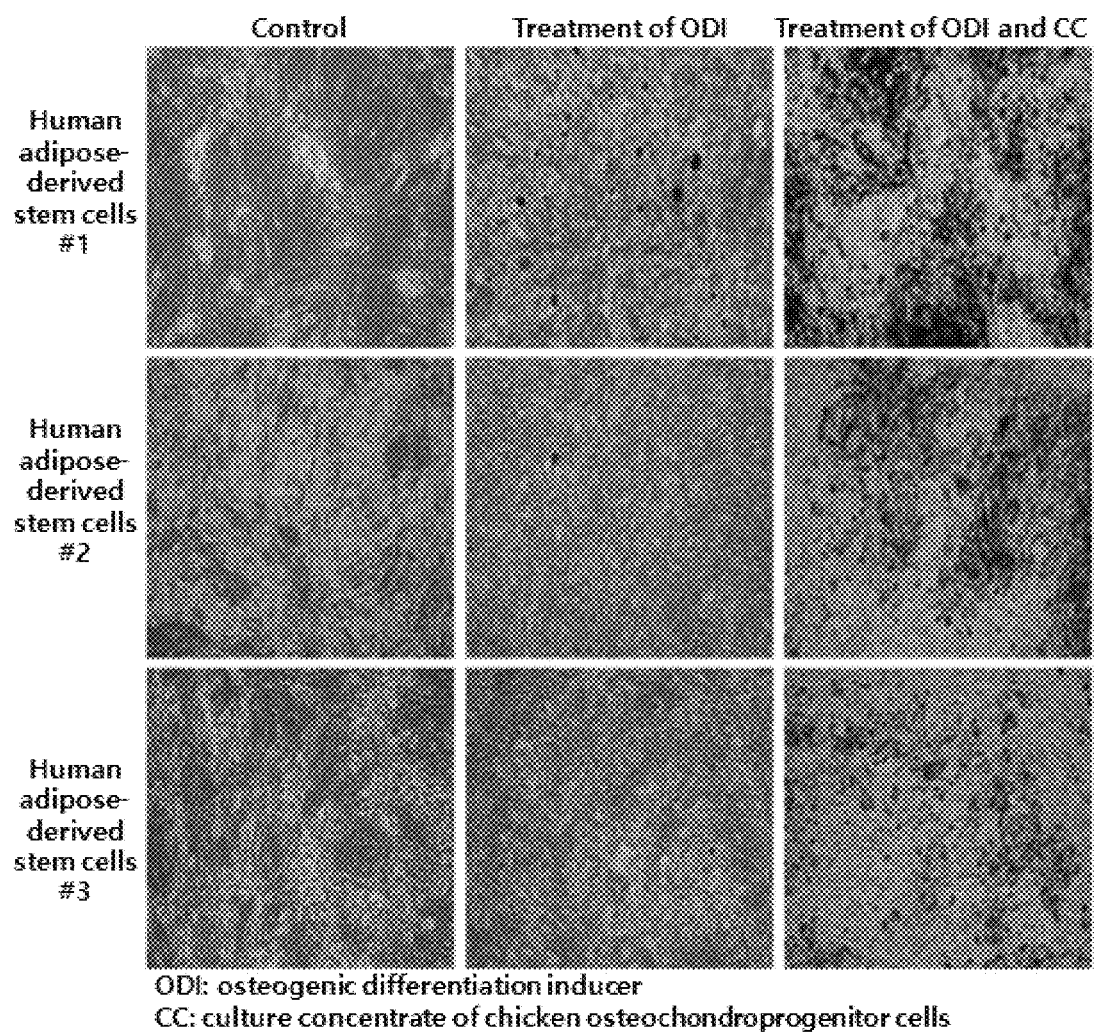
FIG. 5 illustrates the results of confirming the degree of osteogenic differentiation of mesenchymal stem cells cultured in a stem cell culture medium, an osteogenic induction differentiation medium, or an osteogenic induction differentiation medium mixed with a culture concentrate of chicken-derived osteochondroprogenitor cells.

As a result, as illustrated in FIG. 5, it was confirmed that, even all in the adipose tissue-derived mesenchymal stem cells of all three people, the effect of promoting osteogenic differentiation of stem cells was exhibited upon co-treatment with an osteogenic differentiation inducer and the cell concentrate.

Subsequently, to quantify the amount of ARS dyed according to the above experiment, residual water remaining in the container was removed, and then 1 ml of a 10% cetylpyridinium chloride (CPC) buffer, manufactured by Sigma) was added, followed by exposure at room temperature for 30 minutes, to elute ARS. The eluted ARS was dispensed into a 96-well plate (manufactured by SPL) in 200 µl increments, and absorbance at 550 nm was measured using a microplate reader (manufactured by Molecular Devices).

Figure 6A:
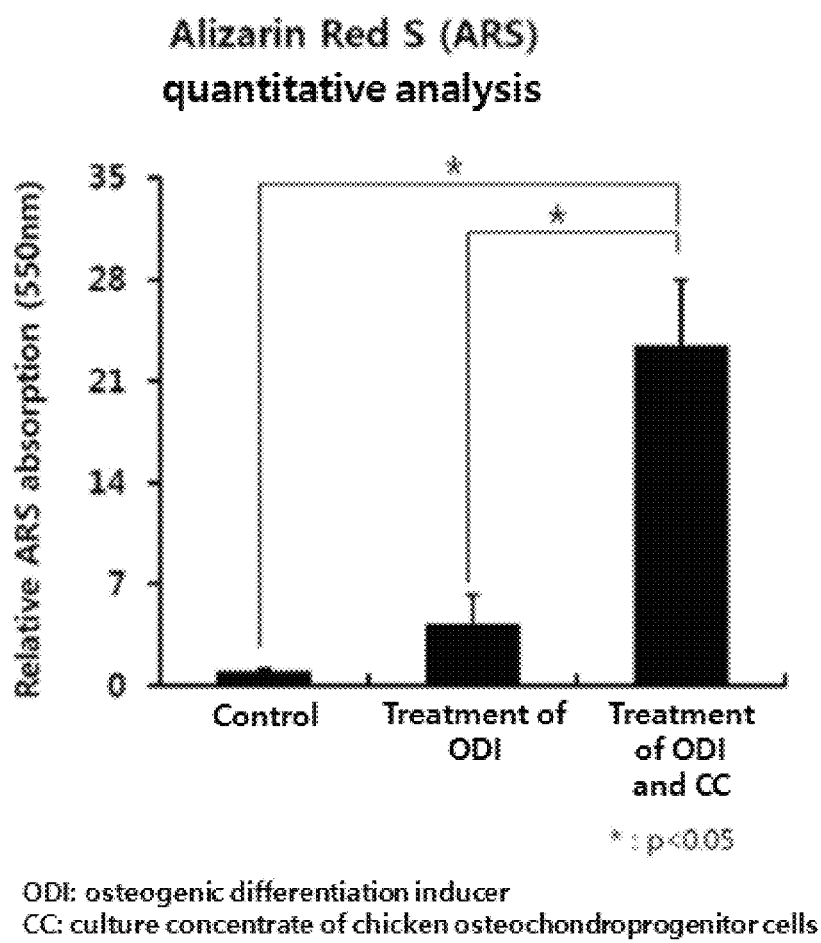
FIG. 6A illustrates the results of quantitatively comparing and confirming the degree of osteogenic differentiation of mesenchymal stem cells cultured in a stem cell culture medium, an osteogenic induction differentiation medium, or an osteogenic induction differentiation medium mixed with a culture concentrate of chicken-derived osteochondroprogenitor cells.

As a result, as shown in FIG. 6A, when the chicken cell culture concentrate was added to the differentiation induction medium, the result of quantitatively and significantly promoting osteogenic differentiation of human mesenchymal stem cells was obtained.

3-3. RUNX2 Gene Analysis

The expression level of the Runx2 gene in the cells of the control, the group treated with an osteogenic differentiation inducer alone, and the group co-treated with an osteogenic differentiation inducer and the culture concentrate alone of Example 3-1 was analyzed using real-time PCR. The Runx2 gene is known to be the most essential transcription factor in osteogenic differentiation. Specifically, RNA was extracted by a phenol-chloroform extraction method using a TRIzol reagent, and cDNA was synthesized using reverse transcription-polymerase chain reaction (RT-PCR), and then real-time PCR was performed using primers specific to the Runx2 gene and the GAPDH gene as a control gene. The information on primers used in PCR is shown in Table 2 below. The results of analyzing relative gene expression levels by electrophoresis of the PCR product on an agarose gel are shown in FIG. 6B.

TABLE 2

| Gene | SEQ ID NO: | Primer base sequence |
|---|---|---|
| human GAPDH | 11 | 5'-gagtcaacggatttggtcgt-3' |
|  | 12 | 5'-ttgattttggagggatctcg-3' |
| human RUNX2 | 13 | 5'-gacagccccaacttcctgt-3; |
|  | 14 | 5'-ccggagctcagcagaataat-3' |

Figure 6B:
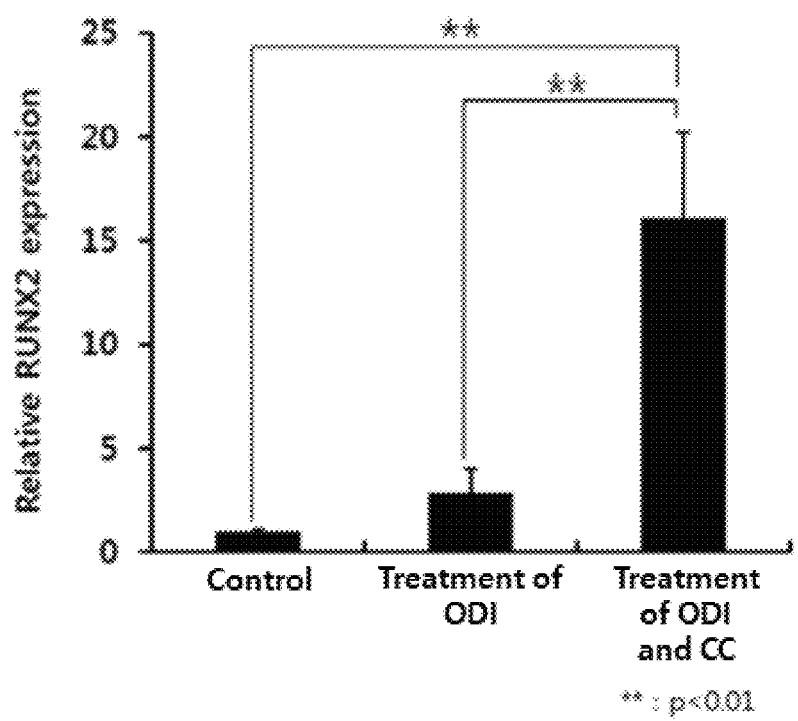
FIG. 6B illustrates the results of confirming the Runx2 gene expression level of mesenchymal stem cells cultured in a stem cell culture medium, an osteogenic induction differentiation medium, or an osteogenic induction differentiation medium mixed with a culture concentrate of chicken-derived osteochondroprogenitor cells.

As a result, as shown in FIG. 6B, it was confirmed that, compared to the control in which no osteogenic differentiation was induced and the group treated with an existing osteogenic differentiation inducer alone, which is commonly used, the expression of the Runx2 gene was significantly increased in the group co-treated with an osteogenic differentiation inducer and the culture concentrate.

From these results, it was confirmed that a culture solution of chicken osteochondroprogenitor cells or a culture concentrate obtained by concentrating the culture solution promotes osteogenic differentiation of human adipose tissue-derived mesenchymal stem cells. Therefore, the present invention provides a composition for promoting osteogenic differentiation of a stem cell using a culture solution of chicken osteochondroprogenitor cells, a method for promoting osteogenesis using the composition, and a bone disease therapeutic agent or adjuvant including the composition. According to the disclosure of the present invention, it can be anticipated that the applicability of stem cell-based therapies to the treatment of various bone diseases is increased, and it is also expected that this will present a novel method of using male chicks as waste resources, which is a global issue.

Example 4. Test for Induction of Chondrogenic Differentiation of Human Adipose Tissue-Derived Mesenchymal Stem Cells In order to perform an experiment for inducing chondrogenic differentiation of the human adipose tissue-derived mesenchymal stem cells acquired in Example 2, the culture concentrate prepared according to Example 1 was added to a stem cell culture medium (DMEM medium containing 10% FBS and 1% antibiotic) at a concentration of 100 µg/ml. As a positive control, a DMEM medium supplemented with 1×ITS, 1.25 mg/ml of BSA, 5 µg/ml of linoleic acid, 50 µg/ml of ascorbic acid-2-phosphate, 10 ng/ml of TGF-β1, 10% FBS, and 1% antibiotic was used.

4-1. Chondrogenic Differentiation Induction

The human adipose tissue-derived mesenchymal stem cells at 5 passages were put into a 15 ml conical tube (manufactured by SPL) at a density of 2 to 2.5×10$^5$ cells, and then precipitated by centrifugation at 320 G for 1 minute to form a pellet. Chondrogenic differentiation was performed by culturing the pellet in each of three media for 10 days, and the media were replaced once every 3 days. Alcian blue staining was used to confirm whether chondrogenic differentiation occurred.

1) Negative control: Non-induction culture medium (stem cell culture medium); 2) Positive control: TGF-β1-based chondrogenic induction differentiation medium; and 3) Experimental group: chondrogenic induction differentiation medium to which only 100 µg/ml of the culture concentration of Example 1-6 was added to the stem cell culture medium.

4-2. Confirmation of Chondrogenic Differentiation through Alcian Blue Staining

Alician blue can be used to determine chondrogenic differentiation through staining in blue when 4% or more of cysteine is contained in the sulfated glycosaminoglycan of the cartilage matrix, or proteins. A pellet was recovered 10 days after induction of chondrogenic differentiation using the method of Example 4-1, washed three times with DPBS, and immersed in 4% paraformaldehyde (PFA) at room temperature for 24 hours. The fixed pellet was subjected to clearing and dehydration, and then embedded in paraffin. Cell sections were made with a thickness of 6 µm using a sectioning machine, and the prepared sections were deparaffinized and hydrated, and then maintained in an Alcian blue solution for 30 minutes for staining. At this time, the Alcian blue solution was prepared by diluting 1% Alcian blue powder in an acetic acid solution and adjusting a pH thereof to 2.5 with 1/10 N HCl. Subsequently, after washing for 5 minutes under running water, the pellet sections were treated with a 0.1% Nuclear Fast Red Solution for 2 minutes. The Nuclear Fast Red Solution was prepared by stirring 0.1% Nuclear Fast Red Solution powder and 5% aluminum sulfate powder in distilled water. After washing for 5 minutes under running water, the product was mounted through dehydration and clearing. The stained cell pellet was photographed after confirming Alician blue staining under an optical microscope, and the stained portion of the captured cell pellet image was quantified using the ImageJ program.

Figure 7A:
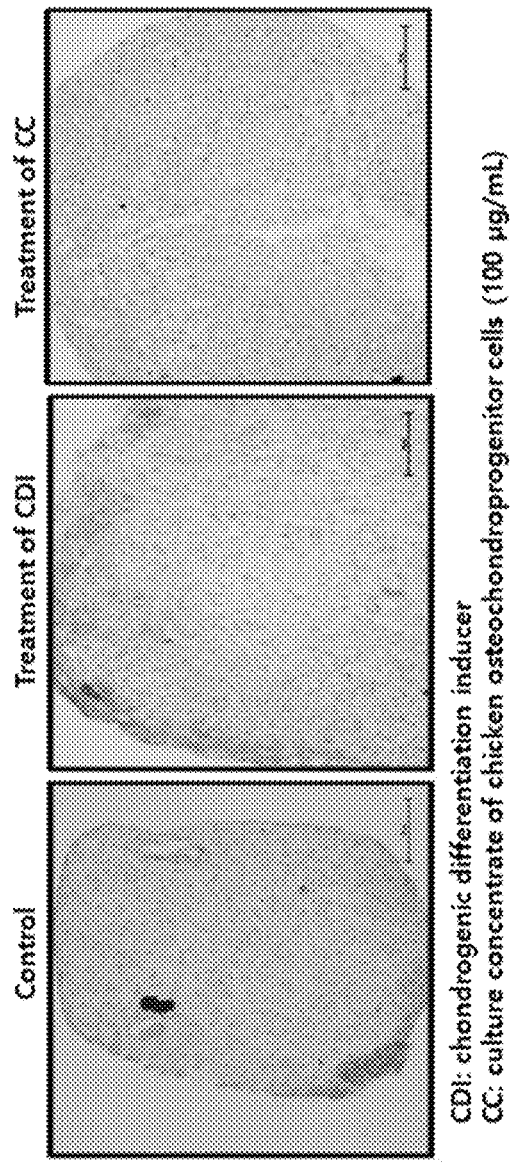
FIG. 7A illustrates the result of confirming differentiation of human adipose tissue-derived stem cells into chondrocytes according to treatment with a culture concentrate of chicken-derived osteochondroprogenitor cells.
Figure 7B:
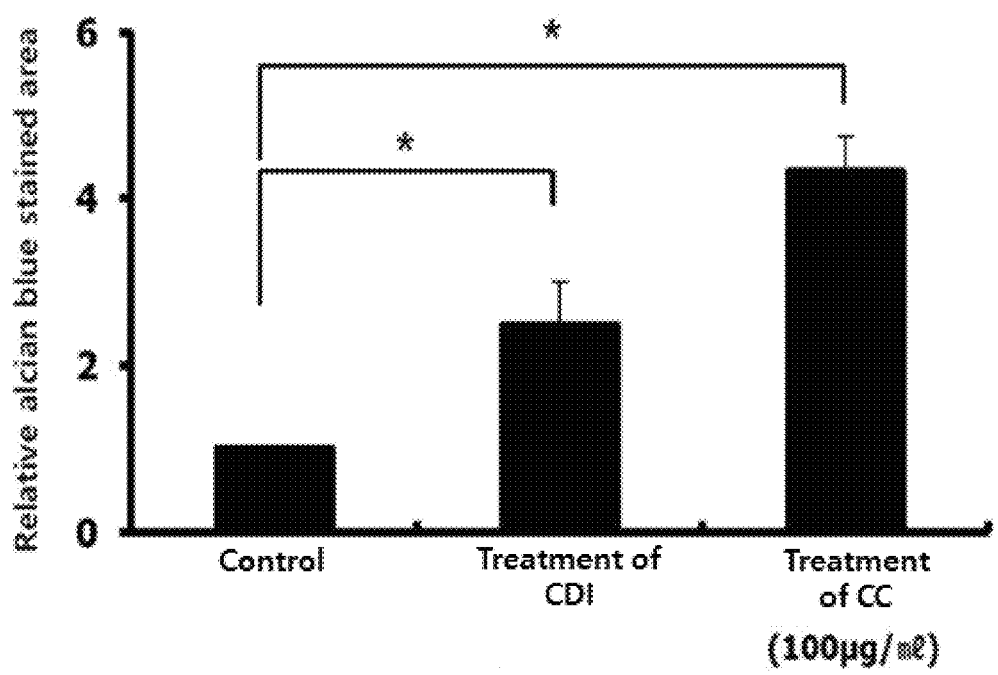
FIG. 7B illustrates the result of confirming that the culture concentrate of chicken-derived osteochondroprogenitor cells can be used as a chondrogenic differentiation inducer.

As a result, as illustrated in FIG. 7A, it was confirmed that, upon treatment with 100 µg/ml of the culture concentrate alone, large amounts of sulfated glycosaminoglycans of the cartilage matrix stained with Alcian blue, or 4% or more cysteine-containing proteins were observed, from which it was confirmed that chondrogenic differentiation of stem cells was induced by the chicken cell culture concentrate. In addition, as illustrated in FIG. 7B, it was confirmed that the culture concentrate is an inducer capable of inducing chondrogenic differentiation of human adipose-derived stem cells. The above results suggest that the chicken cell culture concentrate can be used as a novel material for inducing differentiation, which replaces existing chondrogenic differentiation inducers.

4-3. Confirmation of Expression of Cartilage-Related Proteins Sox9, Aggrecan, and ColII Sox9, Aggrecan, and Collagen type II (ColII) are proteins capable of confirming whether chondrogenic differentiation of stem cells occurs. To re-confirm whether the chicken cell culture concentrate of the present invention induces chondrogenic differentiation of stem cells, the expression of Sox9, Aggrecan, and ColII of stem cells treated with the culture concentrate was examined. Specifically, a pellet was recovered 10 days after induction of chondrogenic differentiation using the method of Example 4-1, washed three times with DPBS, and fixed in 4% paraformaldehyde (PFA) at room temperature for 24 hours. The fixed pellet was subjected to clearing and dehydration, and then embedded in paraffin. Cell sections were made with a thickness of 6 μm using a sectioning machine, and the prepared cell sections were exposed to a heating block at 60° C. for 45 minutes to perform deparaffinization. Subsequently, washing three times with xylene for 5 minutes, three times with 100% ethanol for 5 minutes, twice with 95% ethanol for 2 minutes, twice with 70% ethanol for 2 minutes, and twice with distilled water for 2 minutes were performed, and the washed cell sections were treated with an antigen unmasking solution (manufactured by Vector), followed by treatment with a 9:1 mixture of 100% methanol and 30% hydrogen peroxide for 10 minutes. Subsequently, the cell sections were washed three times with PBS and blocked with PBS supplemented with 1% BSA and 10% goat serum at room temperature for 1 hour. Each protein was treated with primary antibodies to cause a reaction at 4° C. for 18 hours, and then washed three times with PBS and treated with biotinylated anti-IgG at room temperature for 1 hour. After washing three times again with PBS, the protein was treated with streptavidin-HRP at room temperature for 45 minutes. A reaction was allowed to occur using 3,3-diaminobenzidine (DAB) for 1 minute to develop a color. The color development was confirmed using an optical microscope and it was confirmed whether protein expression occurred, and the results thereof are shown in FIG. 8.

Figure 8:
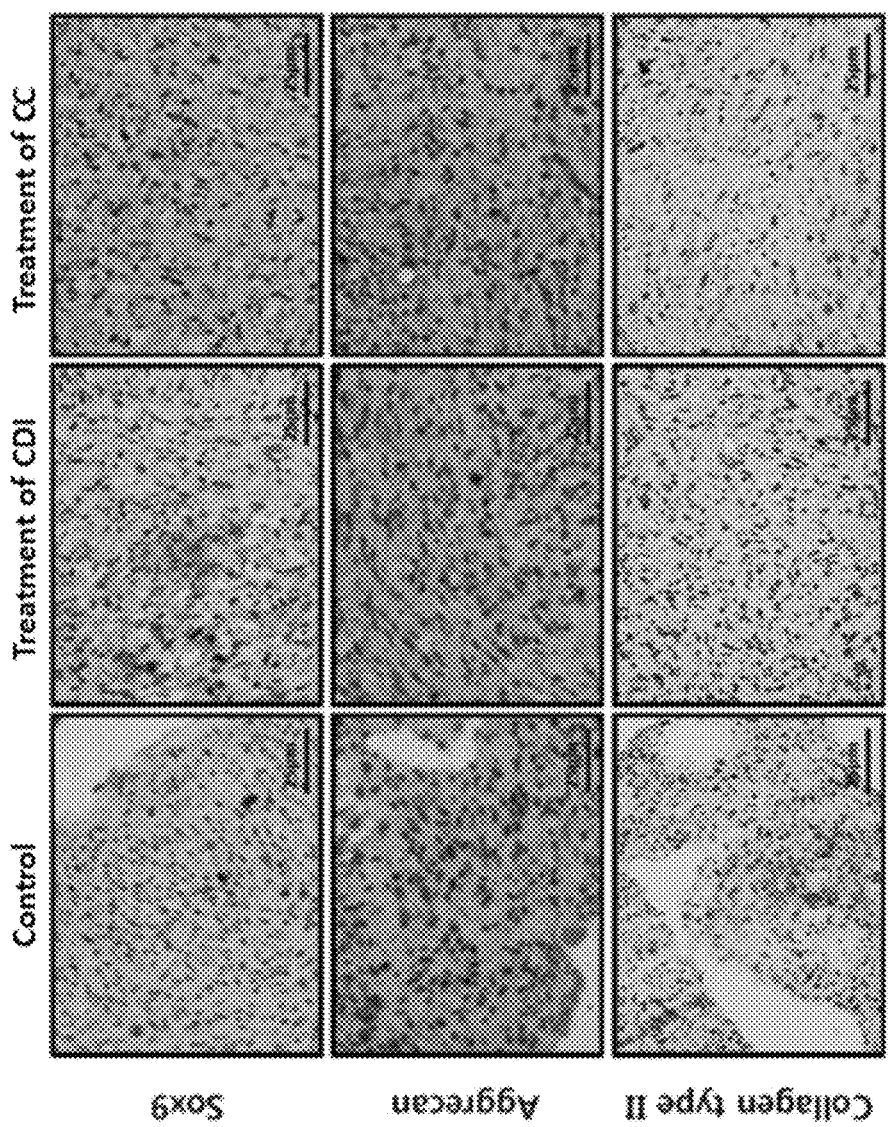
FIG. 8 illustrates staining results of proteins used to confirm whether chondrogenic differentiation occurs, such as Sox9, Collagen type I (Col I), and Collagen type II (ColII).

As a result, as illustrated in FIG. 8, it was confirmed that, compared to the negative control, chondrogenic differentiation-related proteins Sox9, Aggrecan, and ColII were expressed in the experimental group treated with the culture concentrate at a level as high as in the positive control.

From the above results, it is derived that the cell culture solution obtained by culturing chicken osteochondroprogenitor cells induces chondrogenic differentiation of human adipose tissue-derived mesenchymal stem cells. The present invention has the potential to be developed as a therapeutic agent or adjuvant for cartilage disease using a culture solution of chicken osteochondroprogenitor cells, and is expected to present a novel method of using male chicks as waste resources, which is global issue.

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

A culture solution or culture concentrate of chicken bone marrow-derived osteochondroprogenitor cells, according to the present invention, can be used as an agent for treating bone damage diseases requiring new bone formation or regeneration, such as osteoporosis, bone defect diseases, Paget's disease, femoral head avascular necrosis, and osteoarthritis, an adjuvant, and a health functional food for bone health, and is expected to be applicable as an agent for treating cartilage damage diseases requiring new cartilage formation or regeneration, such as degenerative arthritis, rheumatoid arthritis, fractures, damage to muscle tissue, plantar fasciitis, humerus epicondylitis, calcifying myositis, joint damage due to non-union or trauma of the fracture, an adjuvant, and a health functional food for joint health.

The invention claimed is:

1. A method of promoting osteogenic differentiation efficiency of a stem cell or inducing chondrogenic differentiation of a stem cell, comprising treating the stem cell with a culture solution of chicken bone marrow-derived osteochondroprogenitor cells.

2. The method of claim 1, wherein the chicken is a starter chick.

3. The method of claim 1, wherein the culture solution of chicken bone marrow-derived osteochondroprogenitor cells is a culture concentrate.

4. The method of claim 1, further comprising treating the stem cell with an osteogenic differentiation inducer.

5. The method of claim 1, wherein the stem cell is a mesenchymal stem cell.

6. The method of claim 1, wherein the treatment of the stem cell with a culture solution of chicken bone marrow-derived osteochondroprogenitor cells is performed by culturing the stem cell in a medium comprising the culture solution of chicken bone marrow-derived osteochondroprogenitor cells.

7. A method of preventing or treating a bone disease, cartilage damage, or a cartilage defect disease comprising administering to a subject in need thereof, a composition comprising a culture solution or culture concentrate of chicken bone marrow-derived osteochondroprogenitor cells as an active ingredient.

8. A method of preventing or treating cartilage damage or cartilage defect disease comprising administering to a subject in need thereof a composition comprising a stem cell as an active ingredient, wherein the stem cell is induced in differentiation by the method of claim 1.

9. A method of preventing or treating cartilage damage or a cartilage defect disease comprising administering to a subject in need thereof a composition comprising a differentiated chondrocyte as an active ingredient, wherein the differentiation is by the method of claim 1.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer of beta actin

<400> SEQUENCE: 1
atgaagccca gagcaaaaga                                                   20

<210> SEQ ID NO 2
<211> LENGTH: 20
<212> TYPE: DNA
<213> ORGANISM: Artificial Sequence
<220> FEATURE:
<223> OTHER INFORMATION: primer of beta actin
```

```
<400> SEQUENCE: 2
ggggtgttga aggtctcaaa                                            20

<210> SEQ ID NO 3
<211> LENGTH: 20
<212> TYPE: DNA
<213> ORGANISM: Artificial Sequence
<220> FEATURE:
<223> OTHER INFORMATION: primer of Sox9

<400> SEQUENCE: 3
gctttctcgc atgaatctcc                                            20

<210> SEQ ID NO 4
<211> LENGTH: 20
<212> TYPE: DNA
<213> ORGANISM: Artificial Sequence
<220> FEATURE:
<223> OTHER INFORMATION: primer of Sox9

<400> SEQUENCE: 4
ttggggaagg tgttctcttg                                            20

<210> SEQ ID NO 5
<211> LENGTH: 20
<212> TYPE: DNA
<213> ORGANISM: Artificial Sequence
<220> FEATURE:
<223> OTHER INFORMATION: primer of Collagen type1

<400> SEQUENCE: 5
caaaccaggc gaaaggggtc                                            20

<210> SEQ ID NO 6
<211> LENGTH: 19
<212> TYPE: DNA
<213> ORGANISM: Artificial Sequence
<220> FEATURE:
<223> OTHER INFORMATION: primer of Collagen type1

<400> SEQUENCE: 6
aatggaccac ggcttccaa                                             19

<210> SEQ ID NO 7
<211> LENGTH: 20
<212> TYPE: DNA
<213> ORGANISM: Artificial Sequence
<220> FEATURE:
<223> OTHER INFORMATION: primer of Collagen type2

<400> SEQUENCE: 7
aagatgttgt aggaccccga                                            20

<210> SEQ ID NO 8
<211> LENGTH: 20
<212> TYPE: DNA
<213> ORGANISM: Artificial Sequence
<220> FEATURE:
<223> OTHER INFORMATION: primer of Collagen type2

<400> SEQUENCE: 8
catctgcgcc gcaaagtttc                                            20

<210> SEQ ID NO 9
<211> LENGTH: 20
```

```
<212> TYPE: DNA
<213> ORGANISM: Artificial Sequence
<220> FEATURE:
<223> OTHER INFORMATION: primer of Runx2

<400> SEQUENCE: 9
cagaccagca gcactccata                                              20

<210> SEQ ID NO 10
<211> LENGTH: 20
<212> TYPE: DNA
<213> ORGANISM: Artificial Sequence
<220> FEATURE:
<223> OTHER INFORMATION: primer of Runx2

<400> SEQUENCE: 10
ttgggcaagt ttgggtttag                                              20

<210> SEQ ID NO 11
<211> LENGTH: 20
<212> TYPE: DNA
<213> ORGANISM: Artificial Sequence
<220> FEATURE:
<223> OTHER INFORMATION: primer of humanGAPDH

<400> SEQUENCE: 11
gagtcaacgg atttggtcgt                                              20

<210> SEQ ID NO 12
<211> LENGTH: 20
<212> TYPE: DNA
<213> ORGANISM: Artificial Sequence
<220> FEATURE:
<223> OTHER INFORMATION: primer of humanGAPDH

<400> SEQUENCE: 12
ttgattttgg agggatctcg                                              20

<210> SEQ ID NO 13
<211> LENGTH: 19
<212> TYPE: DNA
<213> ORGANISM: Artificial Sequence
<220> FEATURE:
<223> OTHER INFORMATION: primer of humanRUNX2

<400> SEQUENCE: 13
gacagcccca acttcctgt                                               19

<210> SEQ ID NO 14
<211> LENGTH: 20
<212> TYPE: DNA
<213> ORGANISM: Artificial Sequence
<220> FEATURE:
<223> OTHER INFORMATION: primer of humanRUNX2

<400> SEQUENCE: 14
ccggagctca gcagaataat                                              20
```